US010607733B2

(12) United States Patent
Reddy

(10) Patent No.: US 10,607,733 B2
(45) Date of Patent: Mar. 31, 2020

(54) SYSTEM AND METHOD FOR ENSURING MEDICAL BENEFIT CLAIM PAYMENT NEUTRALITY BETWEEN DIFFERENT DISEASE CLASSIFICATION CODES

(71) Applicant: SYNTEL, INC., Troy, MI (US)

(72) Inventor: Murlidhar Reddy, Maharashtra (IN)

(73) Assignee: Syntel, Inc., Troy, MI (US)

( * ) Notice: Subject to any disclaimer, the term of this patent is extended or adjusted under 35 U.S.C. 154(b) by 1148 days.

(21) Appl. No.: 14/306,208

(22) Filed: Jun. 16, 2014

(65) Prior Publication Data

US 2014/0372142 A1  Dec. 18, 2014

Related U.S. Application Data

(60) Provisional application No. 61/834,908, filed on Jun. 14, 2013.

(51) Int. Cl.

| | |
|---|---|
| *G16H 40/20* | (2018.01) |
| *G06F 19/00* | (2018.01) |
| *G06Q 50/22* | (2018.01) |
| *G06F 8/70* | (2018.01) |
| *G06F 8/30* | (2018.01) |
| *G16H 10/60* | (2018.01) |

(52) U.S. Cl.
CPC .............. *G16H 40/20* (2018.01); *G06F 8/30* (2013.01); *G06F 8/70* (2013.01); *G06F 19/328* (2013.01); *G06Q 50/22* (2013.01); *G16H 10/60* (2018.01)

(58) Field of Classification Search
CPC ...... G06Q 50/22; G06Q 50/24; G06F 19/328; G06F 8/30; G06F 8/70; G16H 40/20

USPC ........................................................... 705/2
See application file for complete search history.

(56) References Cited

U.S. PATENT DOCUMENTS

| | | | |
|---|---|---|---|
| 4,558,413 A | 12/1985 | Schmidt et al. | |
| 5,018,067 A * | 5/1991 | Mohlenbrock | ....... G06F 19/328 128/920 |
| 6,493,871 B1 | 12/2002 | McGuire et al. | |
| 6,785,410 B2 * | 8/2004 | Vining | .............. G06F 17/30256 382/128 |

(Continued)

OTHER PUBLICATIONS

Stein, Brian D., et al., "The Validity of International Classification of Diseases, Ninth Revision, Clinical Modification Diagnosis Codes for Identifying Patients Hospitalized for COPD Exacerbations." Chest Journal 141.1 (2012), pp. 87-93.

(Continued)

*Primary Examiner* — Hiep V Nguyen
(74) *Attorney, Agent, or Firm* — Miles & Stockbridge, P.C.

(57) ABSTRACT

A neutrality analysis system includes receives existing claim data including at least one existing healthcare code associated with a first classification system, receives new claim data including a plurality of new healthcare codes associated with a second classification system, wherein the at least one existing healthcare code is mapped to the at least one new healthcare code, receives a plurality of payment codes associated with the at least one existing healthcare code and the at least one new healthcare code, and based on the received plurality of payment codes, calculates payments of the received existing and new claim data, respectively, and based on the calculating, selects a financially neutral new healthcare code of the plurality of new healthcare codes.

20 Claims, 26 Drawing Sheets

(56) References Cited

U.S. PATENT DOCUMENTS

| | | |
|---|---|---|
| 7,233,938 B2 | 6/2007 | Carus et al. |
| 7,437,302 B2 | 10/2008 | Haskell et al. |
| 7,546,595 B1 | 6/2009 | Wickham et al. |
| 7,861,239 B2 | 12/2010 | Mayfield et al. |
| 8,265,952 B1 | 9/2012 | Smith |
| 8,370,799 B2 | 2/2013 | Nir-Buchbinder et al. |
| 8,428,970 B1 | 4/2013 | Fiferlick |
| 2003/0069760 A1 | 4/2003 | Gelber |
| 2003/0191665 A1 | 10/2003 | Fitzgerald et al. |
| 2004/0172291 A1* | 9/2004 | Knowlton ............. G06Q 10/10 705/2 |
| 2005/0038670 A1* | 2/2005 | Takkar ................. G06Q 10/10 705/2 |
| 2005/0137912 A1 | 6/2005 | Rao et al. |
| 2007/0027720 A1 | 2/2007 | Hasan et al. |
| 2008/0195999 A1 | 8/2008 | Cohen et al. |
| 2009/0150181 A1 | 6/2009 | Gejdos et al. |
| 2009/0164252 A1 | 6/2009 | Morris et al. |
| 2010/0094657 A1 | 4/2010 | Stern |
| 2010/0198799 A1 | 8/2010 | Krishnan et al. |
| 2011/0301982 A1 | 12/2011 | Green, Jr. et al. |
| 2012/0078979 A1 | 3/2012 | Ghimire |
| 2012/0089964 A1 | 4/2012 | Sawano |
| 2012/0254083 A1 | 10/2012 | Patrao et al. |
| 2012/0296675 A1 | 11/2012 | Silverman |
| 2012/0311426 A1 | 12/2012 | Desai et al. |
| 2013/0035947 A1* | 2/2013 | Sundararam .......... G06Q 50/22 705/2 |
| 2013/0073301 A1* | 3/2013 | Rao ...................... G06Q 40/08 705/2 |
| 2013/0144651 A1 | 6/2013 | Rao |
| 2013/0185094 A1 | 7/2013 | Mukerji et al. |
| 2013/0227524 A1 | 8/2013 | Im et al. |
| 2013/0227533 A1 | 8/2013 | Tonkin et al. |
| 2014/0136495 A1 | 5/2014 | Kottaram |

OTHER PUBLICATIONS

McDonald, Clement J., et al. "Open Source Software in Medical Informatics—Why, How and What." International Journal of Medical Informatics 69.2 (2003), pp. 175-184.

Ayewah, Nathaniel, et al. "Evaluating Static Analysis Defect Warnings on Production Software", Proceedings of the 7th ACM SIGPLAN-SIGSOFT Workshop on Program Analysis for Software Tools and Engineering, ACM, (2007), pp. 1-7.

Coder Coach: "What the Heck is a DRG? And Why Should I Care About Case Mix?" (Jan. 6, 2011, 5 pgs.).

"Introduction to Network Load Balancing", Network Load Balancing (NLB) (Jan. 21, 2005, 2 pgs.).

"Overview of Network Load Balancing" (Dec. 21, 2007, 3 pgs.).

Ron Mills, "ICD-10-CM/PCS MS-DRG Grouper Part 1" (May 23, 2011, 3 pgs.).

Non Final Office Action dated Apr. 15, 2019 in U.S. Appl. No. 14/306,060.

Final Office Action dated Jun. 27, 2019 in U.S. Appl. No. 14/306,077.

Final Office Action dated Aug. 1, 2019 in U.S. Appl. No. 14/306,060.

3M "Advanced Analyzer Software" Apr. 2013 (Year: 2013).

De, Suman "8 Steps to Success in ICD-10-CM/PCS Mapping: Best Practices to Establish Precise Mapping Between Old and New ICD Code Sets" as downloaded from http://library.ahima.org/doc?oid=106975 Journal of AHIMA 83, No. 6 (Jun. 2012): 44-49. (Year: 2012).

3M TM "Coding and Reimbursement System" Published Apr. 2013 (Year: 2013).

CMS, "General Equivalence Mappings—ICD-9-CM to and from ICD-10-CM and ICD-10-PCS" Mar. 2009 (Year: 2009).

Cognizant, "ICD Code Crosswalks: No Substitute for ICD-10 Compliance" cognizant 20-20 insights I May 2013 (Year: 2013).

Non Final Office Action dated Jan. 13, 2020 in corresponding U.S. Appl. No. 14/306,077.

Quest Software, Toad for Oracle User Guide 10, 2009, Quest Software, pp. 1-8, 185-186 and 197.

Non Final Office Action dated Jan. 28, 2020 in corresponding U.S. Appl. No. 14/306,060.

* cited by examiner

Data Preparation | Data Management | Data Execution | Data Verification | Data Analytics | Logout
*502* — *504* — *506* — *520* — *508* — *510*

Type Of Neutrality Testing: [SELECT ▽]
- FINANCIAL NEUTRALITY (FNT)
- BENEFIT NEUTRALITY (BNT)
- BOTH (BOTH)

- Field Mapping
- Upload File
- Reconciliation
- Export Data
- Audit Trail

Field Mapping

File Type Mapping Template: [Claim Header Template ▽]

[Download Template]  [Upload Mapping]  [View Mapping]

| | | | Reconciliation | | | | |
|---|---|---|---|---|---|---|---|
| Field Mapping | | | | | | | |
| Upload File | Customer Name: | FNProjectDemo ▼ | | Select Iteration | 3 ▼ | | |
| Reconciliation | Reconciliation failed. Below given are the details of reconciliation failure. | | | | | | |
| Export Data | | | | Get Reconciliation Report | | | |
| Audit Trail | | | | | | | |

Claims missing in ICD9 file

| | | | | | | | Export to Excel |
|---|---|---|---|---|---|---|---|

| MEMBER ID | CLAIM NUMBER | PRIMARY DIAGNOSIS CODE | PROCEDURE CODE | DRG CODE | ALLOWED AMOUNT | MEMBER RESPONSIBILITY AMOUNT | DEDUCTIBLE AMOUNT |
|---|---|---|---|---|---|---|---|
| 9521478 | 916015005100 | J84.10 | 9925 | 895 | 5007.19 | | 0 |
| 2985471 | 916015005107 | D50.9 | 9915 | 895 | 1127.00 | | 0 |
| 3333146 | 916015005112 | R11.2 | 9918 | 895 | 1109.50 | | 0 |
| 624557 | 916015005115 | R11.2 | 9913 | 895 | 5007.19 | | 0 |
| 3319414 | 916015005120 | J84.10 | 9925 | 895 | 1171.81 | | 0 |
| 3348914 | 916015005123 | R06.00 | 9918 | 895 | 979.96 | | 0 |

*FIG. 8*

Audit Trail Report

Customer Name: SampleProjRNTHoag   Iteration: 1

Export to Excel

AuditTrail Report

| Iteration # | ICD Code Set | File Number | Version | Valid Count | Upload Type | Prioritized Count | User Id | |
|---|---|---|---|---|---|---|---|---|
| ☐ 1 | ICD9 | 1 | 1 | 5 | Newly added | 0 | 1 | 4/24/ |

Field Mapping
Upload File
Reconciliation
Export Data
Audit Trail

*FIG. 10*

| Configuration ▸ | Reports ▸ | Type Of Neutrality Testing | Financial Neutrality (FNT) ▾ | CustomerName | Select ▾ |

◁ ◁ [1] of 2 ▷ ▷|    Page Width ▾    Find | Next [     ]    ▾ Export    🖶

DRG Code in ICD-10  — 1902

| DRG Code | No Of Claims |
|---|---|
| 775 | 101 |
| 982 | 2 |
| 989 | 2 |
| 988 | 1 |
| Total | 106 |

DRG Code Report  — 1904

| DRG Code ⇕ | ICD-9-Diag codes ⇕ | ICD-9- Proc codes ⇕ | Allowed Amount variance ⇕ | No of Claims ⇕ | % Claims ⇕ |
|---|---|---|---|---|---|
| 775 | 645.11 | 73.59 | 18196.43 | 10 | 9.43 |
| 775 | 659.61 | 75.62 | 5224.66 | 1 | 0.94 |
| 775 | 664.21 | 73.59 | 4113.34 | 2 | 1.89 |
| 775 | 664.41 | 73.59 | 0.00 | 1 | 0.94 |
| 775 | 665.51 | 73.59 | 0.00 | 1 | 0.94 |
| 775 | 669.51 | 72.79 | 0.00 | 1 | 0.94 |
| 775 | 671.81 | 73.6 | 0.00 | 1 | 0.94 |
| 775 | 642.31 | 75.69 | 0.00 | 1 | 0.94 |
| 775 | 644.21 | 73.59 | 0.00 | 4 | 3.77 |

Type Of Neutrality Testing: Benefit Neutrality (BNT)   CustomerName: E2ETesting10   Configuration   Reports Iteration: 1   |◁ ◁ 1 of 1 ▷ ▷|   Amount Type: Allowed Amount   Page Width ▼   Find | Next   Select a format ▼   Export   View Report

Top 15 DRG Codes for ICD-9 and ICD-10

☐ Not Present in ICD-9   ☒ Not Present in ICD-10
⇕ ICD-10 Allowed Amount Decreased   ⇕ ICD-10 Allowed Amount Increased   ⇔ ICD-9 and ICD-10 Allowed Amount Equal

| DRG Code ICD-9 | DRG Description | % Payment | | DRG Code ICD-10 | DRG Description | % Payment |
| --- | --- | --- | --- | --- | --- | --- |
| 248 | Perc cardiovasc proc w non-drug-eluting stent w MCC or 4+ ves/stens | 36.76 | | 250 | Perc cardiovasc proc w/o coronary artery stent w MCC | 49.42 |
| 247 | Perc cardiovasc proc w drug-eluting stent w/o MCC | 33.62 | | 251 | Perc cardiovasc proc w/o coronary artery stent w/o MCC | 40.67 |
| 246 | Perc cardiovasc proc w drug-eluting stent w MCC or 4+ vessels/stents | 10.77 | | 981 | Extensive O.R. procedure unrelated to principal diagnosis w MCC | 2.52 |
| 003 | ECMO or trach w MV 96+ hrs or PDX exc face, mouth & neck w maj O.R. | 4.92 | | 237 | Major cardiovasc procedures w MCC or thoracic aortic aneurysm repair | 2.14 |
| 251 | Perc cardiovasc proc w/o coronary artery stent w/o MCC | 4.83 | | | | |
| 249 | Perc cardiovasc proc w non-drug-eluting stent w/o MCC | 4.59 | | | | |
| 981 | Extensive O.R. procedure unrelated to principal diagnosis w MCC | 2.40 | | | | |
| 237 | Major cardiovasc procedures w MCC or thoracic aortic aneurysm repair | 2.04 | | | | |

FIG. 23

SYSTEM AND METHOD FOR ENSURING MEDICAL BENEFIT CLAIM PAYMENT NEUTRALITY BETWEEN DIFFERENT DISEASE CLASSIFICATION CODES

CROSS-REFERENCE TO RELATED APPLICATION

This application claims the benefit of, and priority to, U.S. Patent Application Ser. No. 61/834,908, filed Jun. 14, 2013, the disclosure of which is incorporated herein by reference in its entirety.

FIELD OF THE INVENTION

This disclosure relates generally to a computerized system and method for healthcare-related data, and more specifically to a system and method for testing medical benefit claims for neutrality of such claims between different disease classification codes such as between ICD-9 and ICD-10 code sets.

BACKGROUND

Healthcare legislation specifies procedures for communicating information within the healthcare industry. For example, Title II (Administrative Simplification provisions) of the Health Insurance Portability and Accountability Act of 1996 ("HIPAA") required the Department of Health and Human Services to establish national standards for electronic health care transactions and national identifiers for providers, health plans, and employers.

On Jan. 1, 2012, an updated version of the healthcare transactions standard, HIPAA 5010, replaced version 4010A1, the current set of standards. Among various changes in this update, HIPAA 5010 mandates changes to the International Classification of Diseases ("ICD"), which is a nomenclature for the classification of diseases, injuries, and other medical conditions. More specifically, HIPAA 5010 requires healthcare payers and providers to transition from the current International Classification of Diseases, 9th Revision, Clinical Modification ("ICD-9") to a 10th revision ("ICD-10"). This transition is referred to herein as the "ICD-10 migration" and, at present, all healthcare stakeholders (e.g., providers, payers, and employers), must make this transition by Oct. 1, 2015.

ICD-10 codes exhibit fundamental differences as compared with ICD-9 codes. For example, the form and information conveyed in ICD-10 codes is different than that of the ICD-9 codes. More specifically, ICD-9 codes contain three to five digits beginning with either a number or a letter, with a decimal point placed after the third digit, and the ICD-9 book indicates the level of specificity for each code. ICD-10 codes, on the other hand, are seven digits in length. The first three digits of the ICD-10 codes are similar to the ICD-9 codes, with a decimal point after the third digit. However, the digits that follow the decimal point have different, specific meanings. For medical and surgical procedures, for example, the digits that follow are specific to body part, surgical approach, and other qualifiers needed for billing. Similarly, the ICD-10 codes that represent diagnosis codes also have seven digits.

The first three digits of ICD-10 codes are similar to the ICD-9 code, but the additional digits add specificity to the code such as laterality, chronic versus acute, and so on. Another significant difference between the ICD-9 and ICD-10 code sets is the number of codes. More specifically, ICD-9 includes just over 14,000 diagnosis codes and almost 4,000 procedural codes. In contrast, ICD-10 contains over 68,000 diagnosis codes (clinical modification codes) and over 72,000 procedural codes. Due to such fundamental differences, mapping or translation from the ICD-9 code set to the ICD-10 code set presents challenges to ICD-10 migration. For example, while there are some one-to-one correspondences between ICD-9 and ICD-10 codes, there are also one-to-many, many-to-one and many-to-many correspondences and, in some cases, no correspondence at all. Accordingly, ICD-10 migration will undoubtedly affect many aspects of information collection, reporting requirements, billing and payment systems, potentially resulting in benefit, financial and clinical variations.

SUMMARY

The present invention may comprise one or more of the features recited in the attached claims, and/or one or more of the following features and combinations thereof. In one aspect, a computerized method comprises receiving existing claim data including at least one existing healthcare code associated with a first classification system, receiving new claim data including a plurality of new healthcare codes associated with a second classification system, wherein the at least one existing healthcare code is mapped to the at least one new healthcare code, receiving a plurality of payment codes associated with the at least one existing healthcare code and the at least one new healthcare code, based on the received plurality of payment codes, calculating payments of the received existing and new claim data, respectively, and based on the calculating, selecting a financially neutral new healthcare code of the plurality of new healthcare codes.

In another aspect, a system comprises one or more computing devices including a memory having program code stored therein, and a processor in communication with the memory for carrying out instructions in accordance with the stored program code, wherein the program code, when executed by the processor, causes the processor to perform steps comprising receiving existing claim data including at least one existing healthcare code associated with a first classification system, receiving new claim data including a plurality of new healthcare codes associated with a second classification system, wherein the at least one existing healthcare code is mapped to the at least one new healthcare code, receiving a plurality of payment codes associated with the at least one existing healthcare code and the at least one new healthcare code, based on the received plurality of payment codes, calculating payments of the received existing and new claim data, respectively, and based on the calculating, selecting a most financially neutral new healthcare code of the plurality of new healthcare codes.

In yet another aspect, a computer program product comprising non-transitory computer readable medium further comprising code for receiving existing claim data including at least one existing healthcare code associated with a first classification system, code for receiving new claim data including a plurality of new healthcare codes associated with a second classification system, wherein the at least one existing healthcare code is mapped to the at least one new healthcare code, code for receiving a plurality of payment codes associated with the at least one existing healthcare code and the at least one new healthcare code, based on the received plurality of payment codes, code for calculating payments of the received existing and new claim data, respectively, and based on the calculating, code for selecting a most financially neutral new healthcare code of the plurality of new healthcare codes.

BRIEF DESCRIPTION OF THE DRAWINGS

This disclosure is illustrated by way of example and not by way of limitation in the accompanying FIGS. Where considered appropriate, reference labels have been repeated among the FIG.s to indicate corresponding or analogous elements.

FIG. 5 is an example screen shot illustrating a process for selecting a type of neutrality testing.

FIG. 8 is an example screen shot illustrating a process for reconciling ICD-9 and ICD10 claim files for missing and common claim files.

FIG. 10 is an example screen shot illustrating a process for maintaining an audit log of all upload activities.

FIG. 19 is an example screen shot illustrating an example DRG variance report generated by the tool.

FIG. 21 is an example screen shot illustrating an example drill down aggregate report generated by the tool.

FIG. 23 is an example screen shot illustrating an example heat map report displaying payment percent variances for the most used DRG descriptions with respect to ICD-9 claims and ICD-10 claims.

DETAILED DESCRIPTION OF THE DRAWINGS

Figure 1:
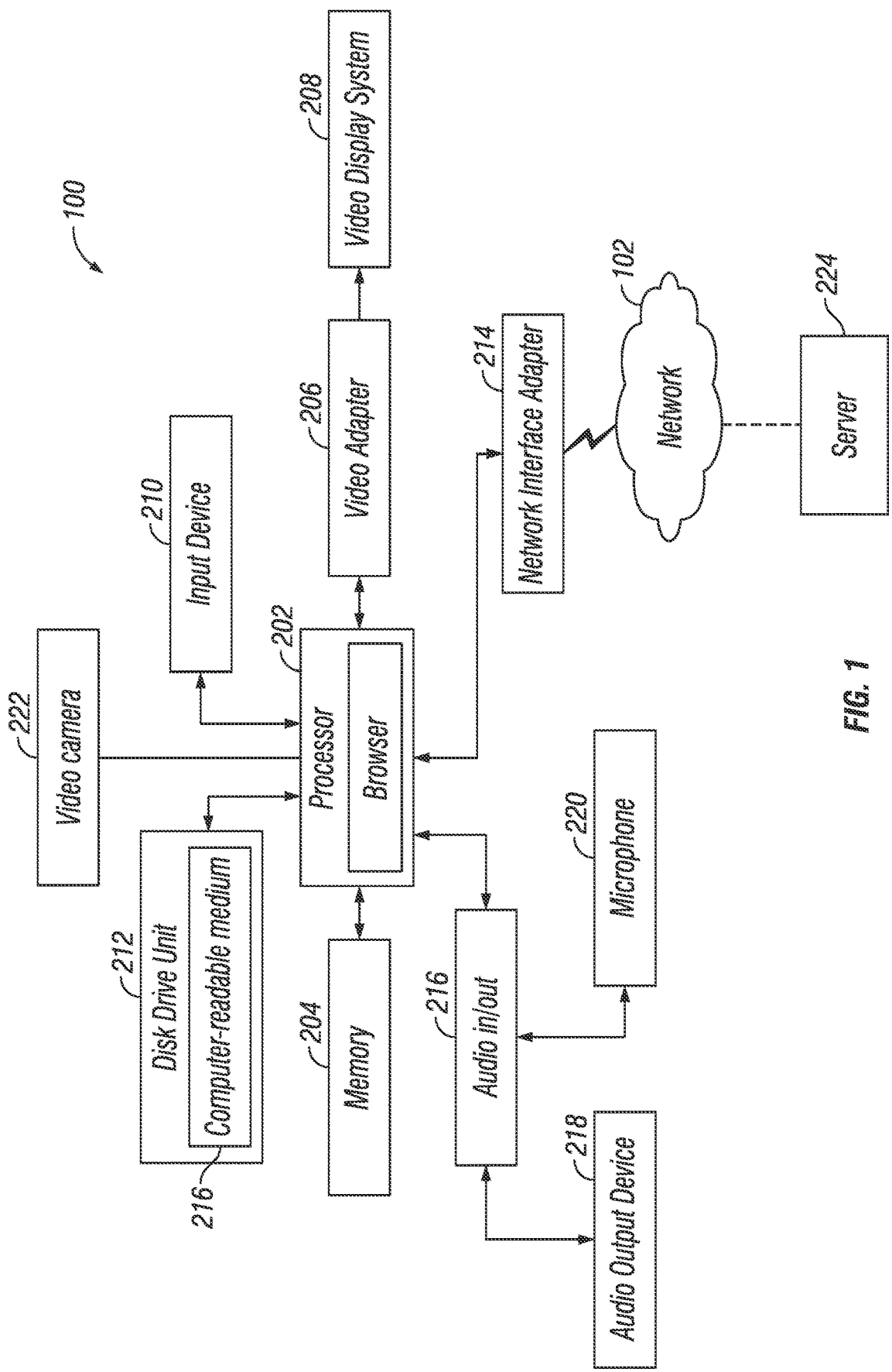
FIG. 1 is a simplified block diagram of an embodiment of a computerized system that may be programmed with a set of instructions to perform any one or more of the functions, processes and methods discussed herein.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

This application relates to the following applications all filed on even date herewith, the disclosures of which are incorporated herein by reference in their entirety; U.S. patent application Ser. No. 14/306,060, entitled System and Method for Providing Mapping Between Different Disease Classification Codes, U.S. patent application Ser. No. 14/306,026, (now U.S. Pat. No. 9,268,907) entitled System and Method for Automatically Modifying Source Code to Accommodate a Software Migration, U.S. patent application Ser. No. 14/305,994, (now U.S. Pat. No. 9,898,582) entitled System and Method for Analyzing an Impact of a Software Code Migration, and U.S. patent application Ser. No. 14/306,077, entitled System and Method for Validating Medical Claim Data.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may or may not necessarily refer to the same embodiment. Further, when a particular feature, structure, process, process step or characteristic is described in connection with an embodiment, it is submitted that it is within the knowledge of one skilled in the art to effect such feature, structure, process, process step or characteristic in connection with other embodiments whether or not explicitly described. Further still, it is contemplated that any single feature, structure, process, process step or characteristic disclosed herein may be combined with any one or more other disclosed feature, structure, process, process step or characteristic, whether or not explicitly described, and that no limitations on the types and/or number of such combinations should therefore be inferred.

Embodiments of this disclosure may be implemented in hardware, firmware, software, or any combination thereof. Embodiments of this disclosure implemented in a computer system may include one or more bus-based interconnects between components and/or one or more point-to-point interconnects between components. Embodiments of this disclosure may also be implemented as instructions stored on one or more machine-readable media, which may be read and executed by one or more processors. A machine-readable medium may be embodied as any device or physical structure for storing or transmitting information in a form readable by a machine (e.g., a computing device). For example, a machine-readable medium may be embodied as any one or combination of read only memory (ROM); random access memory (RAM); magnetic disk storage media; optical storage media; flash memory devices; and others.

Referring now to FIG. 1, an embodiment is shown of a system 100 for ensuring medical benefit claim payment neutrality between different disease classification codes, e.g., between ICD-9 and ICD-10 code sets. Although a migration from ICD-9 to ICD-10 is discussed herein for purposes of example, this disclosure is not intended to be limited to migration from ICD-9 to ICD-10, but encompasses migration from any one medical classification system to another medical classification system. The computing device 100 may be a personal computer, a tablet computer, a personal digital assistant ("FDA"), a media player, a cellular telephone, or any machine capable of executing a set of instructions (sequential or otherwise) that specify actions to be taken. The system 100 according to embodiments of the present disclosure may include a processor 202 (e.g., a central processing unit ("CPU")), a memory 204, a video adapter 206 that drives a video display system 208 (e.g., a liquid crystal display ("LCD"), a cathode ray tube ("CRT"), a touch screen), an input device 210 (e.g., a keyboard, mouse, touch screen display, etc.) for the user to interact with the program (e.g., browser), a disk drive unit 212, a network interface adapter 214, an audio in/out jack 216 that allows audio to be outputted/received by an audio output device 218 (e.g., speaker, headphones) and microphone 220, respectively. Although a combined audio in/out jack 216 is shown for purposes of example, one skilled in the art should appreciate that separate devices may be provided for input and output of audio. It will be understood that that various embodiments of the computing device 100 may not always include all of these peripheral devices, and may instead include various subsets thereof. It will further be understood that the video display system 208 may, in some embodiments, be provided in the form of one or more conventional display monitors.

The disk drive unit 212 includes a computer-readable medium 216 on which may be stored a program code for a web browser with commonly installed plugin(s), such as Flash™ and/or Java™. In some cases, the browser may provide support for the emerging HTML5 WebRTC standard. Embodiments are also contemplated in which the browser could be on a mobile internet connected device, such as a phone or tablet, which has support for the emerging HTML5 WebRTC standard. In one embodiment, a custom application could be provided on an Internet connected mobile device. The term "computer-readable medium" shall be taken to include, but not be limited to, solid-state memories, optical media, flash memory, and magnetic media. Embodiments are contemplated in which the browser may run applications that are received from a server 224 over a network 102 via the network interface device 214 utilizing any one of a number of transfer protocols including but not limited to the hypertext transfer protocol ("HTTP") and file transfer protocol ("FTP"). The network 102 may be any type of packet-switched data network including but not limited to fiber optic, wired, and/or wireless communication capability in any of a plurality of protocols, such as TCP/IP, Ethernet, WAP, IEEE 802.11, or any other protocol.

Compliance with the above discussed migration from ICD-9 to ICD-10 code sets may impact the software and systems of health care providers and payers. Embodiments of the present disclosure are directed to a software testing tool which tests software code used in and with current health care systems for medical claim benefit neutrality between ICD-9 and ICD-10 code sets. Such software source code used in current health care systems may be generically referred to herein as a "codebase."

A primary objective of payers and providers of health care benefits in migrating from ICD-9 to ICD-10 is to avoid payout variations and remain ICD-10 neutral from a financial perspective as well as in key operations such as medical policy enforcement. Claim payment is generally driven by business functions such as benefit configuration, claim adjudication rules, provider contracts, pricing, pre-existing conditions and pre-authorization, and such functions therefore have the potential for high ICD-10 impact.

Health care organizations and health care service organizations alike share an interest in eliminating, or at least mitigating, both financial and benefit-related discrepancies between services covered under ICD-10 as compared with ICD-9. The medical claim benefit neutrality testing tool described herein analyzes differences in provider reimbursement or claims payments by analyzing the impact on provider contracts (e.g., diagnosis related group (DRG) reimbursement technology or case rates) and billing under the ICD-9 and ICD-10 code sets, and further tests benefit parameters to analyze differences in clinical variance due to benefits covered under the ICD-9 and ICD-10 code sets. Such benefit parameters may include, but are not limited to, deductibles, co-insurance costs, co-payment amounts, limit amounts, member visit accumulators, place of service constraints, gender restrictions and age limitations.

Objectives of neutrality testing generally include, but are not necessarily limited to:

1. conducting a financial (reimbursement) risk analysis (testing), benefit risk analysis (testing) and operational risk analysis (testing) to understand and quantify deviations in reimbursement and any impact of member benefits and benefit rules that may result from the migration from the ICD-9 code set to the ICD-10 code set, 2. identifying the cause of any such deviation, which as determining which DRG(s) is/are causing the deviation(s) and, within each identified DRG, which ICD code(s) is/are responsible for deviation(s) that exceed a defined threshold, and using this information to realign ICD-9 to ICD-10 conversion maps to eliminate or at least reduce the variance, 3. identifying which providers are filing claims for those ICD codes identified in 2. above, and formulating a business strategy to mitigate risks associated with the attendant variances, and 4. identifying conditions within various benefit plans for those ICD codes identified in 2. above, and redesigning products and/or services to mitigate risks associated with the attendant variances.

Embodiments of the medical claim benefit neutrality testing tool described herein seek to meet one or more of the above objectives with a single sign-on portal to process various phases of neutrality testing to evaluate the impact on financial and benefit neutrality due to ICD-9 to ICD-10 migration.

Figure 2:
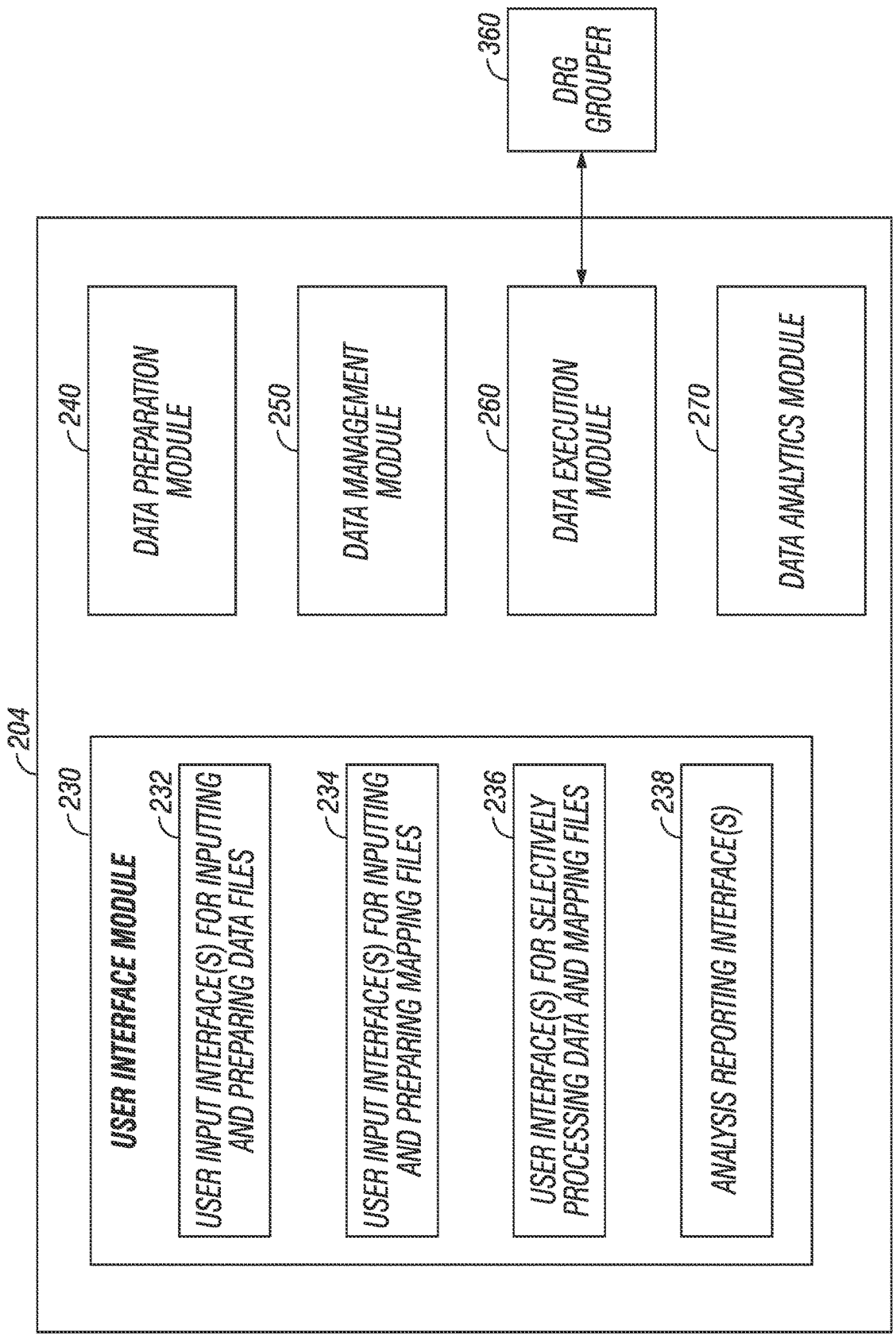
FIG. 2 is a simplified block diagram representation of a medical claim benefit neutrality testing tool executed by the system illustrated in FIG. 1.

Referring now to FIG. 2, a simplified block diagram is shown of a software environment of the system of FIG. 1. In the illustrated embodiment, the medical claim benefit neutrality testing tool is implemented in the form of instructions stored in the memory 204 of the system 100 and executable by the processor 202 to perform the functions described herein. Alternatively or additionally, the instructions may be stored in whole or in part on the computer-readable medium 216, and/or on the server 224 and accessed by the processor 202 via the network 102. Alternatively or additionally still, the server 224 may include one or more processors which execute the instructions, and input/output data may be exchanged between the processor 202 and the server 224 via the network 102. In any case, the medical claim benefit neutrality testing tool includes a user interface module 230, a data preparation module 240, a data management module 250, a data execution module 260 that illustratively communicates with an external DRG grouper 360, and a data analytics module 270.

The user interface module 230 illustratively includes a number of graphic user interfaces via which users of the tool may prepare and input information, e.g., data files, disease classification code mapping files, and the like, into the tool, operate the tool to selective process data and mapping files, and produce reports. In this regard, the user interface module 230 illustratively includes a plurality of graphic user interfaces 232 for preparing and inputting data files. The user interface module 230 further illustratively includes a plurality of graphic user interfaces 234 for preparing and inputting disease classification code mapping files. The user interface module 230 further illustratively includes a plurality of graphic user interfaces 236 for selecting processing data and the mapping files. The user interface module 230 further includes a plurality of graphic user interfaces 238 for creating reports of the analyses conducted by the tool.

The data preparation tool 240 is operable to manage preparation of data files, e.g., claims files and the like, for analysis by the tool. The data management tool 250 is operable to manage information input to the tool and information selection during operation of the tool. The data management module 250 is further operable to manage file transfer within the tool, and to manage data downloads and uploads. The data execution module 260 is operable to process and analyze the data files and mapping files to assess benefit and/or financial neutrality of input data. The data analytics module 270 is operable to analyze the results of the data execution module and produce reports that provide insight into the benefit neutrality and/or financial neutrality of the data being processed by the tool.

Figure 3:
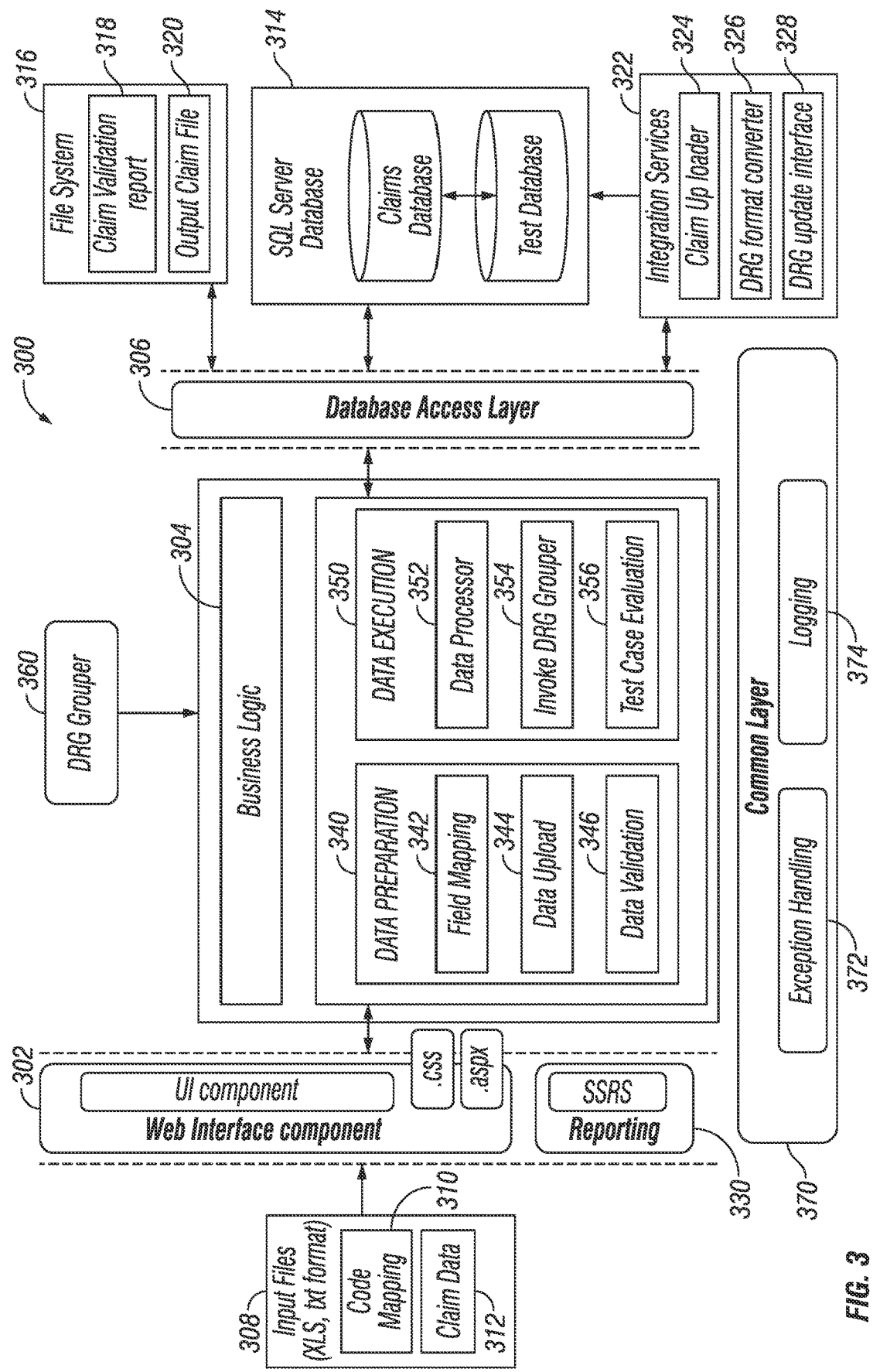
FIG. 3 is a simplified block diagram depicting an example architecture of the medical claim benefit neutrality testing tool.

Referring now to FIG. 3, a simplified diagram is shown illustrating an example architecture 300 of the of the medical claim benefit neutrality testing tool. The medical claim benefit neutrality testing tool architecture includes, but is not limited: to a web interface component 302, a business layer 304, and a data access layer 306.

Illustratively hosted in a web server, the web interface component 302 allows users (e.g., medical coders, claims specialists, and administrators) to access the neutrality system via the UI screens. The web interface component 302 may be implemented in any file type that may comprise a standard web page including but not limited to JavaScript (.js), Java Server Pages (.jsp), stylesheets (.css), images (.gif, .jpg, etc.), and HTML files. This user interface 302 accepts, as inputs, information from an input file source, e.g., code mappings 310 and claims data 312, in various formats including but not limited to spreadsheet (e.g., .xls) and text (.txt).

The system supports different SQL-based relational databases 314 through its data access layer 306, such as Oracle and Microsoft-SQL Server. Such a system database 314 acts as a central repository for all claims and testing related data. Also through the data access layer 306, the system can access any claim validation reports 318 and output claim files 320, as part of another file system 316, for example. The data access layer 306 also provides access to one or more services including but not limited to SQL server integration services 322 in the form of, for example, a claim uploader 324, a DRG format converter 326 and DRG update interface 328. The data access layer 306 transfers this data from the respective databases and systems to other layers as required.

When configured as a neutrality portal, the medical claim benefit neutrality testing tool illustratively specifies a file structure on a database server prior to engaging the tool. Such a file structure should illustratively include a DataPreparation file folder including as sub-folders a Claim TextFile folder and an ExportFile folder, and a DataExecution file folder including as subfolders a ComparatorFiles folder and a TestCase folder. The ComparatorFiles folder should include as sub-folders a ClaimSourceFiles folder, a DRGGrouperinputFormat folder, a DRGGrouperOutputFormat folder and an ErrorFileFolder folder, and the TestCase folder should include as sub-folders a TestCase folder and a TestCaseMapping folder. As part of a master data setup, the list of users accessing the web portal should be created in the database server using SQL Scripts, and Provider Base Rate details containing Provider ID and Base Rate should be inserted into the database using SQL Scripts.

A reporting unit 330 receives input parameters through the web interface component 302 that are required to generate reports. Upon receiving the input parameters, the reporting unit 330 may connect to the data access layer 306 for gathering the data values of the parameters selected by the user for report generation. For the report preparation, the reporting unit 330 may employ SQL server reporting services ("SSRS") for preparing a variety of interactive and printed reports.

The business layer 304 illustratively comprises components that implement the business logic and rules responsible for the functionality of the medical claim benefit neutrality testing tool. These components include, but are not limited to: a data preparation module 340, which is responsible for field mapping 342, data upload 344, and data validation 346, and data execution module (also referred to as the comparator function) 350, which is responsible for data processing 352, invocation of the DRG Grouper 354 and test case evaluation 356. The business layer 304 also includes a data management module (see, e.g., FIGS. 2 and 4) for the sampling and prioritizing of input data, and the business layer 304 further communicates with an external DRG Grouper 360. A common layer 370 includes components for performing exception handling 372 and logging 374.

The above described architecture is designed to support seamless vertical scaling. In the case of high transaction volume and/or requirements for catering to a large user base, the web/application servers can be clustered to deliver the load evenly across servers. Clustering of an Internet information services ("IIS") server with a load balance can serve to balance the load by distributing multiple instances of the application across separate processing machines. A suitable load-balancing algorithm, such as a round-robin algorithm may be employed for load balancing. Also, Microsoft Network Load Balancing ("NLB") can be leveraged for load balancing capabilities. Efficient fail-over and fail back of the transactions and sessions during operation of an application can also be implemented. A fail-over mechanism for web/application servers can be implemented using a hot-stand-by node, which may help to alleviate crashes and service downtime. Accordingly, deployment in a cluster may ensure that there is no single point of failure for any application.

Figure 4:
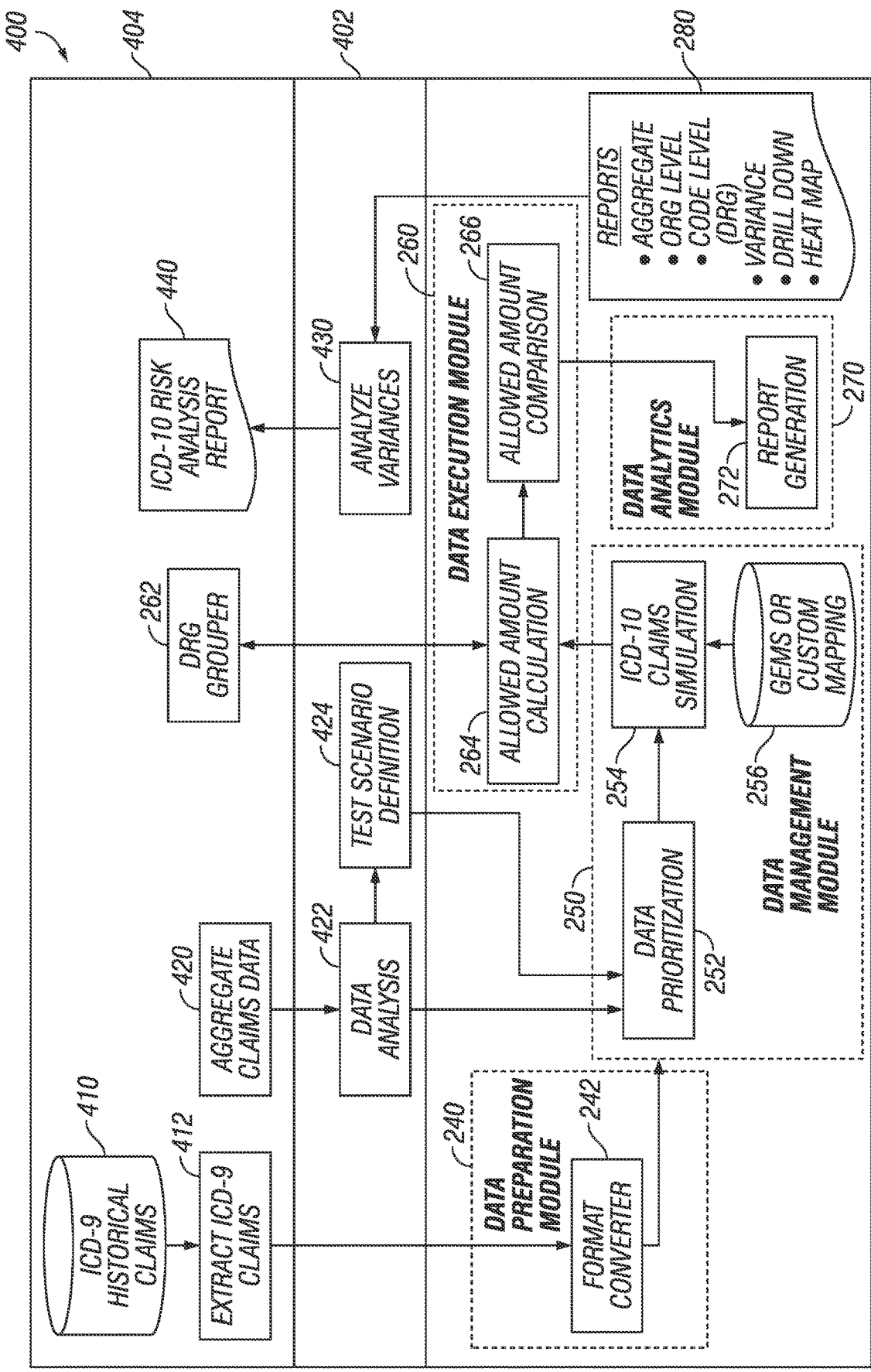
FIG. 4 is simplified block diagram of a financial and benefit risk analysis system 400 of which the medical claim benefit neutrality testing tool of FIGS. 2 and 3 is a part.

Referring now to FIG. 4, a simplified block diagram is shown of a financial and benefit risk analysis system 400 of which the medical claim benefit neutrality testing tool of FIGS. 2 and 3 is a part. In the illustrated embodiment, the data preparation module 240 (see also FIG. 2) illustratively includes a format converter 242 for converting input information to a format suitable for use by the tool. The data preparation module 240 receives historical ICD-9 claims data from a customer database 410 (e.g., as part of a customer system 404), and a customer module 412 extracts a collection or file of ICD-9 claims from the database 410 for analysis by the data medical claim benefit neutrality testing tool.

The data management module 250 (see also FIG. 2) includes a data prioritization feature 252 coupled to a data analysis module 422 and a test scenario definition module 424 of a data analysis service 402. The service 402 receives aggregate claims data from a customer-controlled aggregate claims data source 422, and the service 402 analyzes the claims data and generates test scenarios based on the analyses. Instructions are received from the data analysis module 422 and the test scenario definition module 424 by the data prioritization feature 252, and the data prioritization feature 252 prioritizes and selects data supplied by the data preparation module 240 for analysis. The data prioritization feature illustratively provides test scenario definitions and data to a ICD-10 claims simulation feature 254 which uses GEMs or custom mapping data to supply ICD-9 to ICD-10 forward mappings. The ICD-10 claims simulation data is provided to an allowed calculation amount feature 264 of the data execution module 260, and the allowed amount calculation feature 264 is further coupled to customer-controlled or other off-site DRG Grouper 262. Allowed amounts generated by the allowed amount calculation feature 264 are provided to an allowed amount comparison feature 266 which compares the allowed amounts for variances. A report generation feature 272 of the data analytics module 270 analyzes the allowed amount comparison data produced by the feature 266 and produced reports 280. The reports 280 are analyzed by the service 402 and an ICD-10 risk analysis report 440 is generated therefrom and delivered to the customer 404.

Referring now to FIG. 5, a screen shot is shown of an example user interface 500 following successful login via a login screen of the medical claim benefit neutrality testing tool. In the user interface 500, a user may select a neutrality testing phase to perform. In the illustrated example, the user may select from the following categories of testing phases: data preparation 502, data management 504, data execution 506, data verification 508, and data analytics 510. The above testing phase categories are presented for purposes of example, only. As such, additional categories could be provided; likewise, some of these categories may be optional depending on the circumstances. As shown the data preparation phase 502 is selected.

The example screen shot 500 also shows an options menu 520 for selecting the type of neutrality testing from which a user can choose to have performed. These types include, but are not limited to: financial neutrality testing, benefit neutrality testing, or both. The mapping template for the above-discussed field mappings may vary based on the neutrality type selected.

Figure 6:
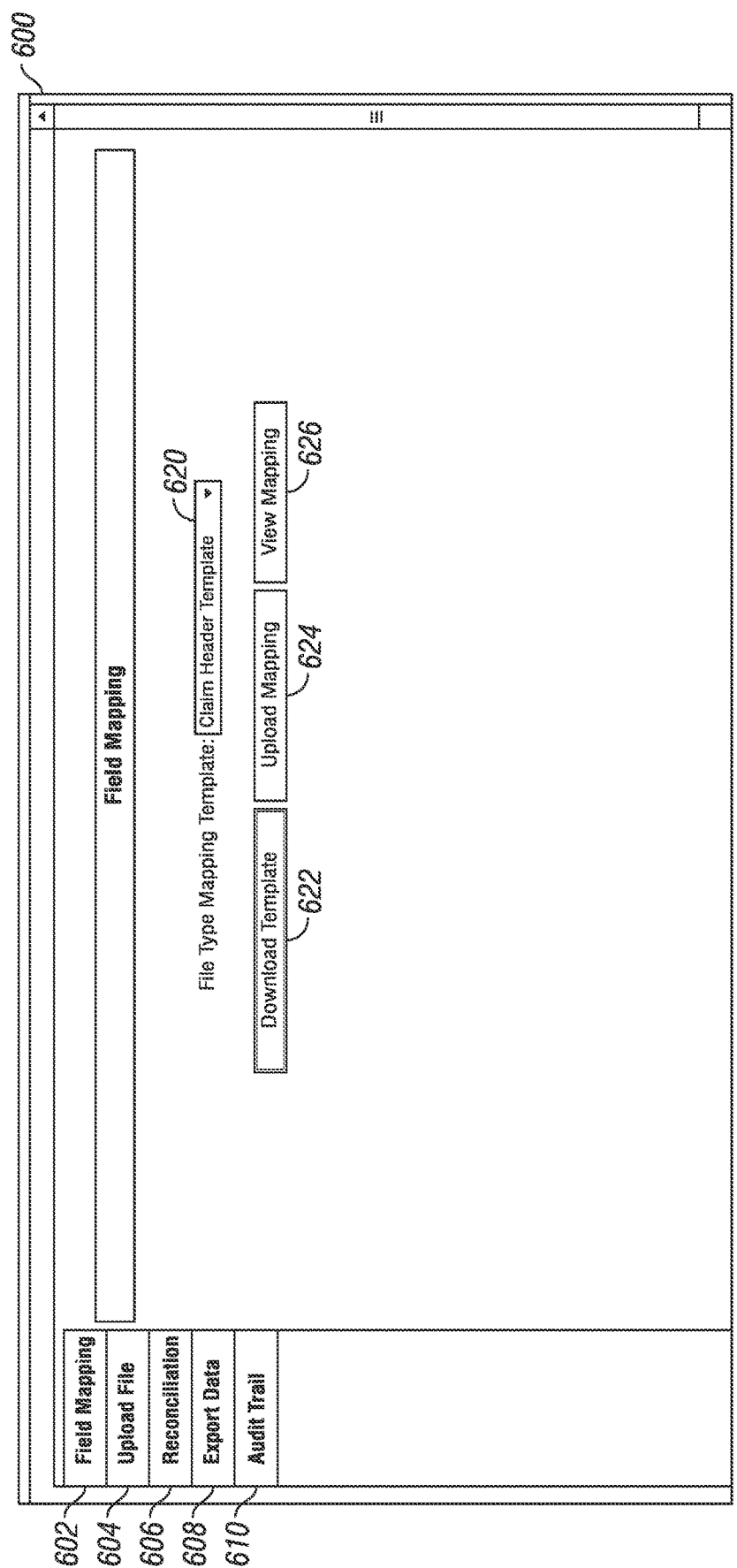
FIG. 6 is an example of a screen shot illustrating a process for defining field mappings for customer claim files.

In the embodiment of the data preparation phase 502 (otherwise known as the format converter tool) shown in FIG. 6, the user may choose to perform the following functions: field mapping 602, upload file 604, reconciliation 606, export data 608, and audit trail 610. In order to perform neutrality testing, the input medical claims data may need to be mapped to the system requirements of the neutrality testing tool. In other words, fields in the claims data may need to be identified that correspond to each of the required input fields of the neutrality testing system. The field mapping function 602 allows a user to define mappings of fields for user fields based on pre-defined fields.

In the example screen shot 600 of FIG. 6, the field mapping function allows a user to download a template 622, upload a mapping 624, and view a mapping 626. By choosing to download a template, the user can download specified mapping templates according to the selected type of neutrality testing he or she wishes to perform (e.g., a financial mapping template or benefit mapping template) using a pull down mapping template selection menu 620. By choosing to upload a mapping 624, the user can load his or her own specific mappings against pre-defined fields from which the user can load his or her ICD-9 and ICD-10 claim header and line level field mapping files.

An example of a financial mapping header template that may be downloaded using the download template button 622 is shown below in Table I.

TABLE I

| Sr No | Customer Field Name | Syntel Field Name | Usage | Unique Identifiers | Data Type | Start Position | End Position |
|---|---|---|---|---|---|---|---|
| 1 | | PLATFORM CODE | Required | | TEXT | | |
| 2 | | MEMBER ID | Required | | TEXT | | |
| 3 | | CLAIM NUMBER | Required | Yes | TEXT | | |
| 4 | | AGE | Optional | | TEXT | | |
| 5 | | GENDER | Required | | TEXT | | |
| 6 | | DOB | Optional | | DATE | | |
| 7 | | PROVIDER ID | Optional | | TEXT | | |
| 8 | | PROVIDER NAME | Optional | | TEXT | | |
| 9 | | PROVIDER TYPE CODE | Optional | | TEXT | | |
| 10 | | PROVIDER STATE CODE | Optional | | TEXT | | |
| 11 | | PROVIDER STATUS CODE | Optional | | TEXT | | |
| 12 | | PROVIDER SPECIALTY VALUE | Optional | | TEXT | | |

TABLE I-continued

| Sr No | Customer Field Name | Syntel Field Name | Usage | Unique Identifiers | Data Type | Start Position | End Position |
|---|---|---|---|---|---|---|---|
| 13 | | CLAIM TYPE | Optional | | TEXT | | |
| 14 | | INPATIENT OUTPATIENT IND | Optional | | TEXT | | |
| 15 | | IN-PLAN NETWORK INDICATOR | Optional | | TEXT | | |
| 16 | | GROUP NUMBER | Optional | | TEXT | | |
| 17 | | AGREEMENT ID | Optional | | TEXT | | |
| 18 | | LINE OF BUSINESS | Optional | | TEXT | | |
| 19 | | BENEFIT PLAN | Optional | | TEXT | | |
| 20 | | ADMIT DATE | Optional | | DATE | | |
| 21 | | DISCHARGE DATE | Optional | | DATE | | |
| 22 | | PLACE OF SERVICE CODE | Required | | TEXT | | |
| 23 | | ADMIT DIAGNOSIS CODE | Optional | | TEXT | | |
| 24 | | PRIMARY DIAGNOSIS CODE | Required | | TEXT | | |
| 25 | | DIAG POA 1 | Required | | TEXT | | |
| 26 | | DIAG CODE 2 | Optional | | TEXT | | |
| 27 | | DIAG POA 2 | Optional | | TEXT | | |
| 28 | | DIAG CODE 3 | Optional | | TEXT | | |
| 29 | | DIAG POA 3 | Optional | | TEXT | | |
| 30 | | DIAG CODE 4 | Optional | | TEXT | | |
| 31 | | DIAG POA 4 | Optional | | TEXT | | |
| 32 | | DIAG CODE 5 | Optional | | TEXT | | |
| 33 | | DIAG POA 5 | Optional | | TEXT | | |
| 34 | | DIAG CODE 6 | Optional | | TEXT | | |
| 35 | | DIAG POA 6 | Optional | | TEXT | | |
| 36 | | DIAG CODE 7 | Optional | | TEXT | | |
| 37 | | DIAG POA 7 | Optional | | TEXT | | |
| 38 | | DIAG CODE 8 | Optional | | TEXT | | |
| 39 | | DIAG POA 8 | Optional | | TEXT | | |
| 40 | | DIAG CODE 9 | Optional | | TEXT | | |
| 41 | | DIAG POA 9 | Optional | | TEXT | | |
| 42 | | DIAG CODE 10 | Optional | | TEXT | | |
| 43 | | DIAG POA 10 | Optional | | TEXT | | |
| 44 | | PROCEDURE CODE 1 | Required | | TEXT | | |
| 45 | | PROCEDURE CODE 2 | Optional | | TEXT | | |
| 46 | | PROCEDURE CODE 3 | Optional | | TEXT | | |
| 47 | | PROCEDURE CODE 4 | Optional | | TEXT | | |
| 48 | | PROCEDURE CODE 5 | Optional | | TEXT | | |
| 49 | | PROCEDURE CODE 6 | Optional | | TEXT | | |
| 50 | | LENGTH OF STAY | Optional | | TEXT | | |
| 51 | | DISCHARGE STATUS CODE | Optional | | TEXT | | |
| 52 | | CLAIM STATUS CODE | Optional | | TEXT | | |
| 53 | | CLAIM REASON CODE | Optional | | TEXT | | |
| 54 | | CLAIM PROGRESS INDICATOR | Required | | TEXT | | |
| 55 | | DRG CODE | Optional | | TEXT | | |
| 56 | | MDC CODE | Optional | | TEXT | | |
| 57 | | CHARGED AMOUNT | Optional | | DECIMAL | | |

TABLE I-continued

| Sr No | Customer Field Name | Syntel Field Name | Usage | Unique Identifiers | Data Type | Start Position | End Position |
|---|---|---|---|---|---|---|---|
| 58 | | ALLOWED AMOUNT | Optional | | DECIMAL | | |
| 59 | | PAID AMOUNT | Optional | | DECIMAL | | |
| 60 | | HEADER HOLDER1 | Optional | | TEXT | | |
| 61 | | HEADER HOLDER2 | Optional | | TEXT | | |
| 62 | | HEADER HOLDER3 | Optional | | TEXT | | |

An example of a financial mapping line template that may be downloaded using the download template button 622 is shown below in Table II.

TABLE II

| Sr No | Customer Field Name | Syntel Field Name | Usage | Unique Identifiers | Data Type |
|---|---|---|---|---|---|
| 1 | | CLAIM NUMBER | Required | Yes | TEXT |
| 2 | | CLAIM LINE NUMBER | Required | Yes | TEXT |
| 3 | | TYPE OF SERVICE | Required | | TEXT |
| 4 | | PLACE OF SERVICE CODE | Optional | | TEXT |
| 5 | | SERVICE CATEGORY | Required | | TEXT |
| 6 | | FIRST DATE OF SERVICE | Optional | | DATE |
| 7 | | LAST PROCEDURE DATE | Optional | | DATE |
| 8 | | REVENUE CODE | Optional | | TEXT |
| 9 | | CPT HCPCS | Optional | | TEXT |
| 10 | | MODIFIER CODE | Optional | | TEXT |
| 11 | | NO OF UNITS | Optional | | TEXT |
| 12 | | CLAIM LINE STATUS CODE | Optional | | TEXT |
| 13 | | CLAIM LINE REASON CODE | Optional | | TEXT |
| 14 | | CLAIM LINE PROGRESS INDICATOR | Optional | | TEXT |
| 15 | | CHARGED AMOUNT | Optional | | DECIMAL |
| 16 | | ALLOWED AMOUNT | Optional | | DECIMAL |
| 17 | | PAID AMOUNT | Optional | | DECIMAL |
| 18 | | EXCLUDE AMOUNT | Optional | | DECIMAL |
| 19 | | LINE HOLDER1 | Optional | | TEXT |
| 20 | | LINE HOLDER2 | Optional | | TEXT |
| 21 | | LINE HOLDER3 | Optional | | TEXT |

An example of a benefit mapping header template that may be downloaded using the download template button 622 is shown below in Table III.

TABLE III

| Sr No | Customer Field Name | Syntel Field Name | Usage | Unique Identifiers | Data Type |
|---|---|---|---|---|---|
| 1 | | PLATFORM CODE | Required | | TEXT |
| 2 | | MEMBER ID | Required | | TEXT |
| 3 | | CLAIM NUMBER | Required | Yes | TEXT |
| 4 | | AGE | Optional | | TEXT |
| 5 | | GENDER | Required | | TEXT |
| 6 | | DOB | Optional | | DATE |
| 7 | | PROVIDER ID | Optional | | TEXT |
| 8 | | PROVIDER NAME | Optional | | TEXT |
| 9 | | PROVIDER TYPE CODE | Optional | | TEXT |
| 10 | | PROVIDER STATE CODE | Optional | | TEXT |
| 11 | | PROVIDER STATUS CODE | Optional | | TEXT |
| 12 | | PROVIDER SPECIALTY VALUE | Optional | | TEXT |
| 13 | | CLAIM TYPE | Optional | | TEXT |
| 14 | | INPATIENT OUTPATIENT IND | Optional | | TEXT |
| 15 | | IN-PLAN NETWORK INDICATOR | Optional | | TEXT |
| 16 | | GROUP NUMBER | Optional | | TEXT |
| 17 | | AGREEMENT ID | Optional | | TEXT |
| 18 | | LINE OF BUSINESS | Optional | | TEXT |
| 19 | | BENEFIT PLAN | Optional | | TEXT |
| 20 | | ADMIT DATE | Optional | | DATE |
| 21 | | DISCHARGE DATE | Optional | | DATE |
| 22 | | PLACE OF SERVICE CODE | Required | | TEXT |
| 23 | | ADMIT DIAGNOSIS CODE | Optional | | TEXT |
| 24 | | PRIMARY DIAGNOSIS CODE | Required | | TEXT |
| 25 | | DIAG POA 1 | Required | | TEXT |
| 26 | | DIAG CODE 2 | Optional | | TEXT |
| 27 | | DIAG POA 2 | Optional | | TEXT |
| 28 | | DIAG CODE 3 | Optional | | TEXT |
| 29 | | DIAG POA 3 | Optional | | TEXT |
| 30 | | DIAG CODE 4 | Optional | | TEXT |
| 31 | | DIAG POA 4 | Optional | | TEXT |
| 32 | | DIAG CODE 5 | Optional | | TEXT |
| 33 | | DIAG POA 5 | Optional | | TEXT |
| 34 | | DIAG CODE 6 | Optional | | TEXT |
| 35 | | DIAG POA 6 | Optional | | TEXT |
| 36 | | DIAG CODE 7 | Optional | | TEXT |
| 37 | | DIAG POA 7 | Optional | | TEXT |
| 38 | | DIAG CODE 8 | Optional | | TEXT |

TABLE III-continued

| Sr No | Customer Field Name | Syntel Field Name | Usage | Unique Identifiers | Data Type |
|---|---|---|---|---|---|
| 39 | | DIAG POA 8 | Optional | | TEXT |
| 40 | | DIAG CODE 9 | Optional | | TEXT |
| 41 | | DIAG POA 9 | Optional | | TEXT |
| 42 | | DIAG CODE 10 | Optional | | TEXT |
| 43 | | DIAG POA 10 | Optional | | TEXT |
| 44 | | PROCEDURE CODE 1 | Required | | TEXT |
| 45 | | PROCEDURE CODE 2 | Optional | | TEXT |
| 46 | | PROCEDURE CODE 3 | Optional | | TEXT |
| 47 | | PROCEDURE CODE 4 | Optional | | TEXT |
| 48 | | PROCEDURE CODE 5 | Optional | | TEXT |
| 49 | | PROCEDURE CODE 6 | Optional | | TEXT |
| 50 | | LENGTH OF STAY | Optional | | TEXT |
| 51 | | DISCHARGE STATUS CODE | Optional | | TEXT |
| 52 | | CLAIM STATUS CODE | Optional | | TEXT |
| 53 | | CLAIM REASON CODE | Optional | | TEXT |
| 54 | | CLAIM PROGRESS INDICATOR | Required | | TEXT |
| 55 | | DRG CODE | Optional | | TEXT |
| 56 | | MDC CODE | Optional | | TEXT |
| 57 | | CHARGED AMOUNT | Optional | | DECIMAL |
| 58 | | ALLOWED AMOUNT | Optional | | DECIMAL |
| 59 | | PAID AMOUNT | Optional | | DECIMAL |
| 60 | | MEMBER RESPONSIBILITY AMOUNT | Optional | | DECIMAL |
| 61 | | DEDUCTIBLE AMOUNT | Optional | | DECIMAL |
| 62 | | MEMBER COPAY TOTAL | Optional | | DECIMAL |
| 63 | | MEMBER COINSURANCE TOTAL | Optional | | DECIMAL |
| 64 | | HEADER HOLDER1 | Optional | | TEXT |
| 65 | | HEADER HOLDER2 | Optional | | TEXT |
| 66 | | HEADER HOLDER3 | Optional | | TEXT |

An example of a benefit mapping header template that may be downloaded using the download template button 622 is shown below in Table IV.

TABLE IV

| Sr No | Customer Field Name | Syntel Field Name | Usage | Unique Identifiers | Data Type |
|---|---|---|---|---|---|
| 1 | | CLAIM NUMBER | Required | Yes | TEXT |
| 2 | | CLAIM LINE NUMBER | Required | Yes | TEXT |
| 3 | | TYPE OF SERVICE | Required | | TEXT |
| 4 | | PLACE OF SERVICE CODE | Optional | | TEXT |
| 5 | | SERVICE CATEGORY | Required | | TEXT |
| 6 | | FIRST DATE OF SERVICE | Optional | | DATE |
| 7 | | LAST PROCEDURE DATE | Optional | | DATE |
| 8 | | REVENUE CODE | Optional | | TEXT |
| 9 | | CPT HCPCS | Optional | | TEXT |
| 10 | | MODIFIER CODE | Optional | | TEXT |
| 11 | | NO OF UNITS | Optional | | TEXT |
| 12 | | CLAIM LINE STATUS CODE | Optional | | TEXT |
| 13 | | CLAIM LINE REASON CODE | Optional | | TEXT |
| 14 | | CLAIM LINE PROGRESS INDICATOR | Optional | | TEXT |
| 15 | | CHARGED AMOUNT | Optional | | DECIMAL |
| 16 | | ALLOWED AMOUNT | Optional | | DECIMAL |
| 17 | | PAID AMOUNT | Optional | | DECIMAL |
| 18 | | EXCLUDE AMOUNT | Optional | | DECIMAL |
| 19 | | MEMBER COINSURANCE AMOUNT | Optional | | DECIMAL |
| 20 | | MEMBER COPAY AMOUNT | Optional | | DECIMAL |
| 21 | | DEDUCTIBLE AMOUNT | Optional | | DECIMAL |
| 22 | | LINE HOLDER1 | Optional | | TEXT |
| 23 | | LINE HOLDER2 | Optional | | TEXT |
| 24 | | LINE HOLDER3 | Optional | | TEXT |

Figure 7:
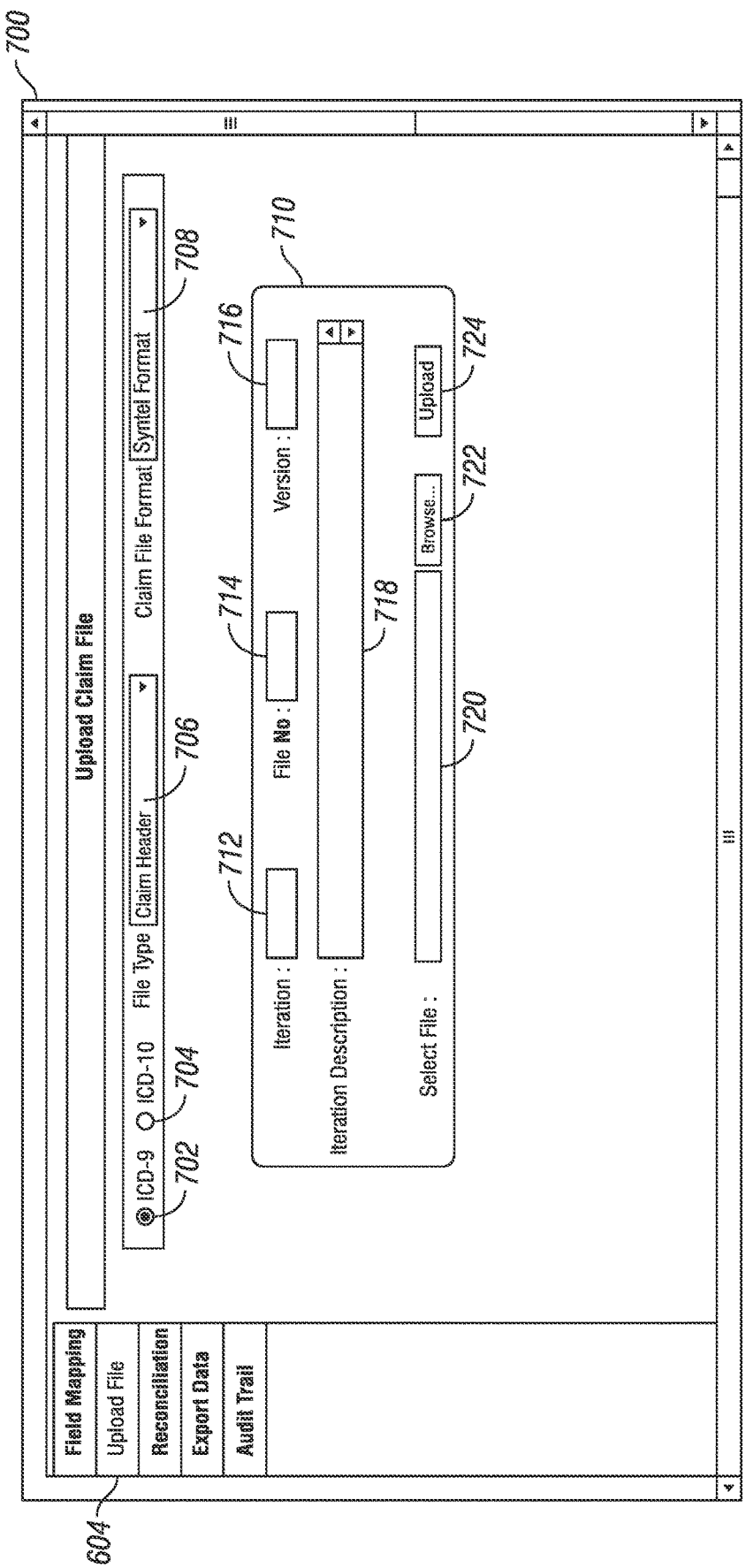
FIG. 7 is an example screen shot illustrating a process for uploading ICD-9 and ICD-10 claims files.

Upon selecting the upload file function, the user could be presented with the interface shown in FIG. 7. On this interface, the user may choose to upload an ICD-9 or ICD-10 claim file through radio buttons 702 and 704 respectively. The system accepts either claim header or claim line file types. For example, selecting "claim header" in the file type drop down box 706 allows the user to upload (and the system to accept) a claim header type claim file. Likewise, selecting "claim line" in the file type drop down box 706 allows the user to upload (and the system to accept) a claim line type claim file.

Based on the previously defined mappings, the system is able to accept different claim file formats. For example, through use of the "claim file format" drop down menu 708, a user can choose to either load claim files per the pre-defined mappings, or to load claim files per user field mappings previously uploaded using the above discussed field mapping functionality.

Embodiments of the present disclosure allow the user to perform neutrality analysis in multiple iterations, or sets of claims. Accordingly, in one embodiment, the neutrality testing tool allows the user to enter various parameters and descriptions related to different iterations through the use of the following fields of a user interface 710: iteration field 712, file number field 714, version field 716, and iteration description field 718. The iteration field 712 allows a user to set an iteration number for the selected neutrality test. The file number field 714 allows the user to set the file number for the given iteration for the selected neutrality test. This feature also allows splitting the claim files in multiple files for different iterations. The version field 716 allows a user to set a version for the entered file number and iteration. Consequently, this allows the system to maintain any revisions to a set of claim files (such as to remove any duplicates or errors such as missing data for required fields, incorrect data types, or invalid diagnosis and procedure codes). The iteration description field 718 allows the user to enter a brief description of the currently loaded claim file.

Embodiments of the present disclosure also employ browsing capabilities. Specifically, a user may browse to a location from which to upload a particular ICD-9 and/or ICD-10 claim file in the select file field 720 (optionally using a browsing function 722). In some cases, the file names follow a naming convention of "CustomerName_xxx.xls", where "CustomerName" refers to the name provided during mapping template upload and "xxx" refers to any other value. However, it is of note that embodiments of the present disclosure are not so limited. It is contemplated that any claim file naming convention may be accepted by the neutrality testing system. Upon uploading the claim files (i.e., through clicking the upload button 724), the system may perform several validation tasks on the claim files.

The tool includes the facility to upload ICD-9 and/or ICD-10 claim records. If an ICD-10 claim file is not available, the tool has a facility to create the ICD-10 claims file from the ICD-9 file.

If both ICD-9 and ICD-10 coded claim files are loaded for the neutrality testing, embodiments of the present disclosure ensure consistency between the files through reconciliation tasks, which can be administered through the use of the system interface, an example screenshot of which is shown in FIG. 8. By selection of the user for which the claim data exists (e.g., through "customer name" drop down menu 802) and the iteration for which reconciliation has not been performed (e.g., through iteration drop down menu 804), the tool can check that the same claim records exist in the ICD-10 claim file as well as the ICD-9 claim file (e.g., by selecting the "get reconciliation report" bar 806). The tool can also check to ensure that the same file types (e.g., claim header and/or claim line) have been uploaded for each ICD-9 and ICD-10 file. For example, if only a claim header type is uploaded for ICD-9 claim files, then the corresponding ICD-10 claim files also may need to be of a claim header type. If any of these checks finds an error, the claim record in the respective file is flagged as not reconciled. In other words, the reconciliation process ensures that both ICD-9 and ICD-10 coded claim files have the same set of claim records according to the unique identifiers defined in the afore-discussed mapping. An example reconciliation report 810 is illustrated in FIG. 8, and the user may export the report 810 to, e.g., an EXCEL™ file using an export button 820.

Figure 9:
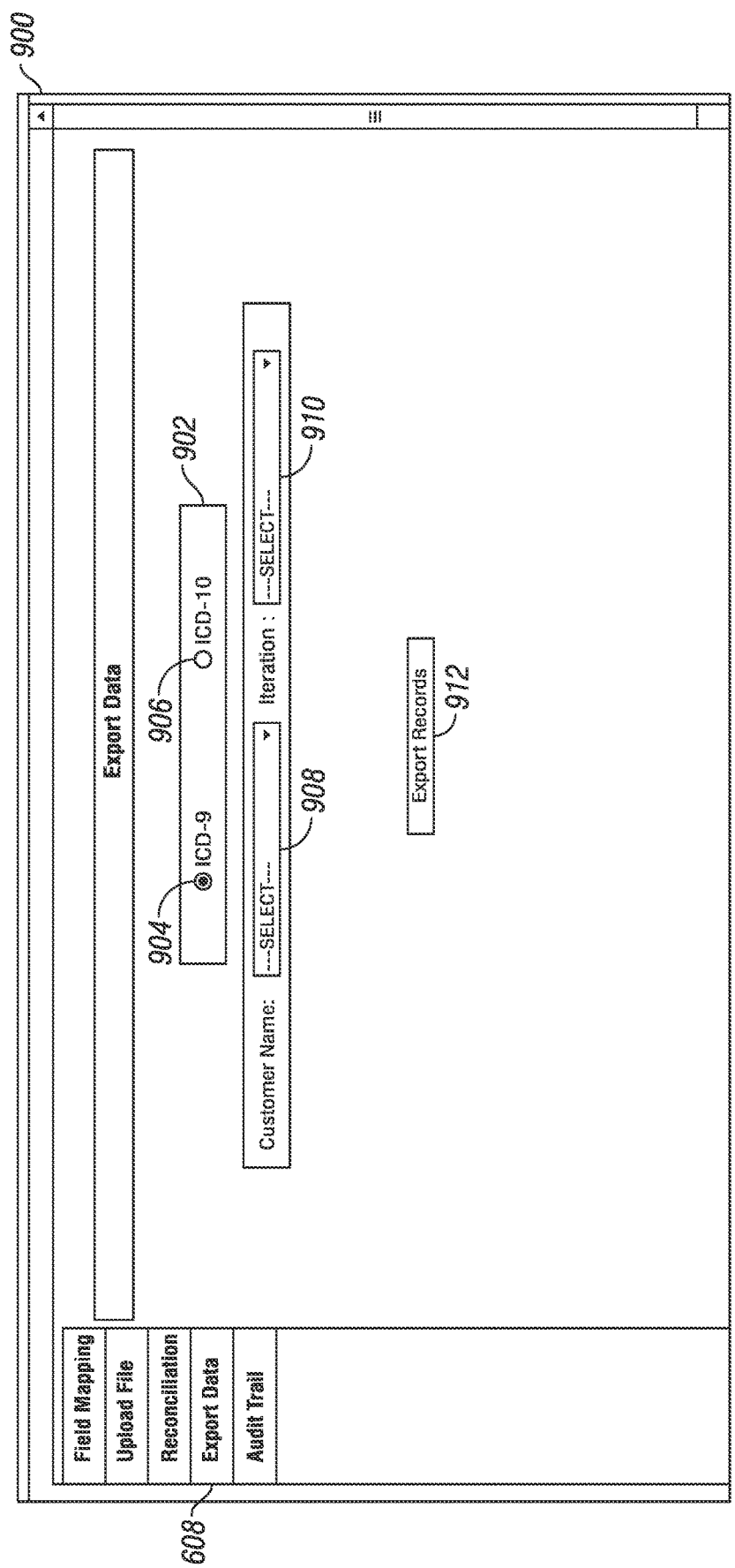
FIG. 9 is an example screen shot illustrating a process for exporting a final set of claims records for use by the tool.

The neutrality testing system allows a user to export data. As shown in the example screen shot of the export data functionality in FIG. 9, the user has the option to: export either an ICD-9 904 or ICD-10 906 claim file, select the customers/payers 908 from which the claim files were originally loaded, and select the iteration 910 for which the claim files were loaded via the above described upload process, and for whom the reconciliation process may have been run. The exporting of records is enabled for a given iteration. The records are exported in split of single or multiple files based on user defined records in the file. If the user clicks on the "Export Records" button 912, link(s) to download claim records are displayed based on the defined records per file for the total number of records in the selected iteration for the selected customer. It should be noted that both the header and line level files may be exported in plain text format.

According to embodiments of the present disclosure, the neutrality testing system includes auditing functionality. Specifically, and as shown in the example screen shot in FIG. 10, by selecting a customer name 1002 and iteration 1004, a user can view accounting details of all records for a desired iteration including: ICD code set type, file type, upload type, file number, version, valid count, prioritized count, and the like.

After being successfully loaded, the files undergo a data management phase of the system. In one embodiment, the data management module 250 illustratively performs the following tasks in this phase of the system: sampling and prioritizing the data, defining risk pools, generating ICD-10 claims data (when only ICD-9 claim file is processed), and performing test case management which includes defining test scenarios, test cases, and mapping them to the claim records.

Figure 11:
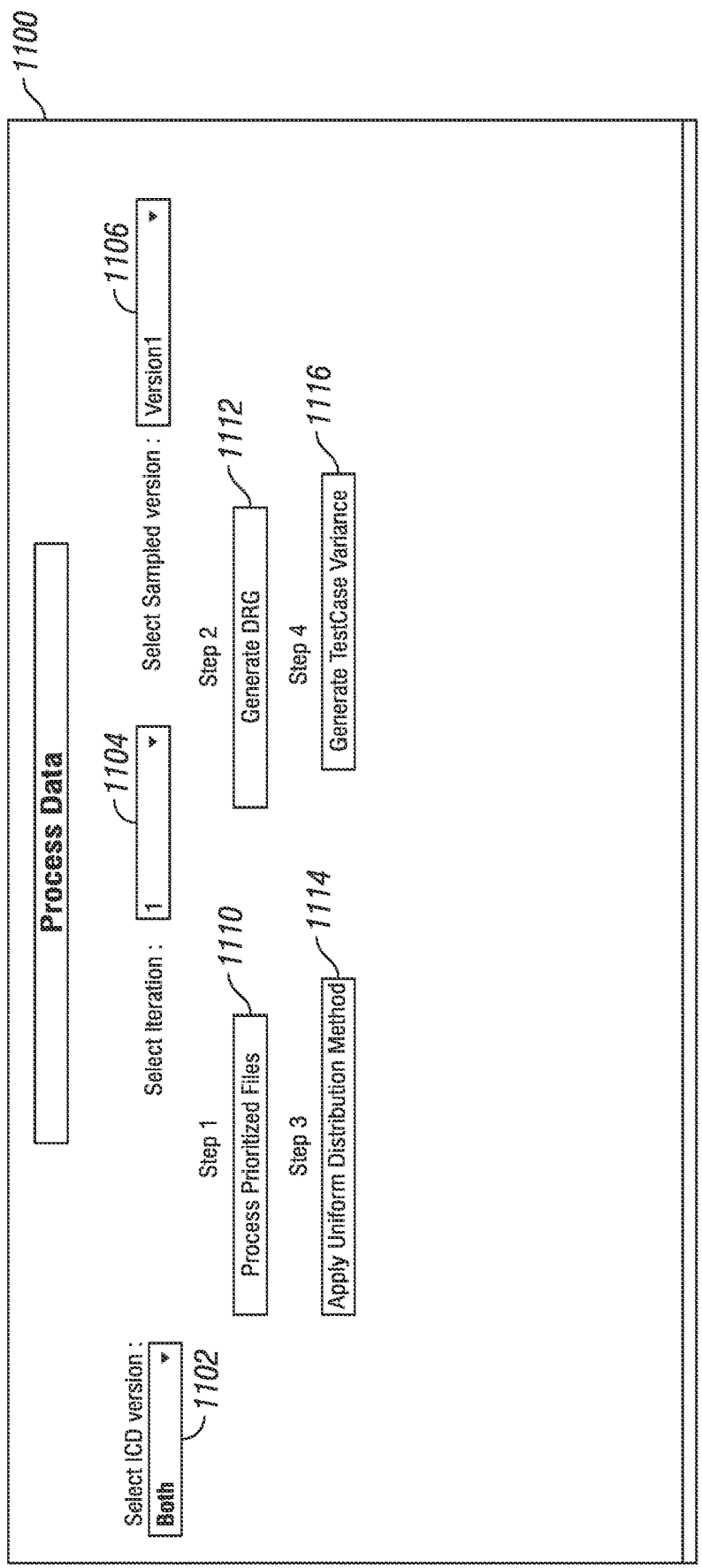
FIG. 11 is an example screen shot illustrating a process for conducting data analysis within the tool.

As shown in the example screen shot in FIG. 11, the data execution module 260, in the data execution phase, loads the prioritized data from the data management module 250 to perform the following functions following selection of an ICD version 1102, an iteration value 1104 and a sampled version 1106:
Processing prioritized files 1110,
Generating DRG codes and weights, and computing allowed amounts 1112,
Applying a Uniform Distribution Method 1114, and
Generating a TestCase variance based on thresholds defined for test cases 1116.

The prioritized ICD-9 and ICD-10 claim files are uploaded with the Customer Name which is illustratively provided with the mapping template. Following processing of the prioritized files 1110, DRG codes and weights are generated 1112 using a grouper tool 360. The grouper tool 360 may take the form of a tool such as the Centers for Medicare and Medicaid Services Medicare Severity Diagnosis Related Groups Grouper (otherwise known as the "CMS MS-DRG Grouper"). The CMS MS-DRG Grouper comprises software that classifies hospital case types into groups expected to have similar hospital resource use. These groupings are based on ICD codes, and other demographic information. These DRG codes and weights, along with updated provider base rate information, can be used to compute an allowed amount (that is, the total amount of money that a medical care provider can ultimately receive for providing a particular service).

Figure 12:
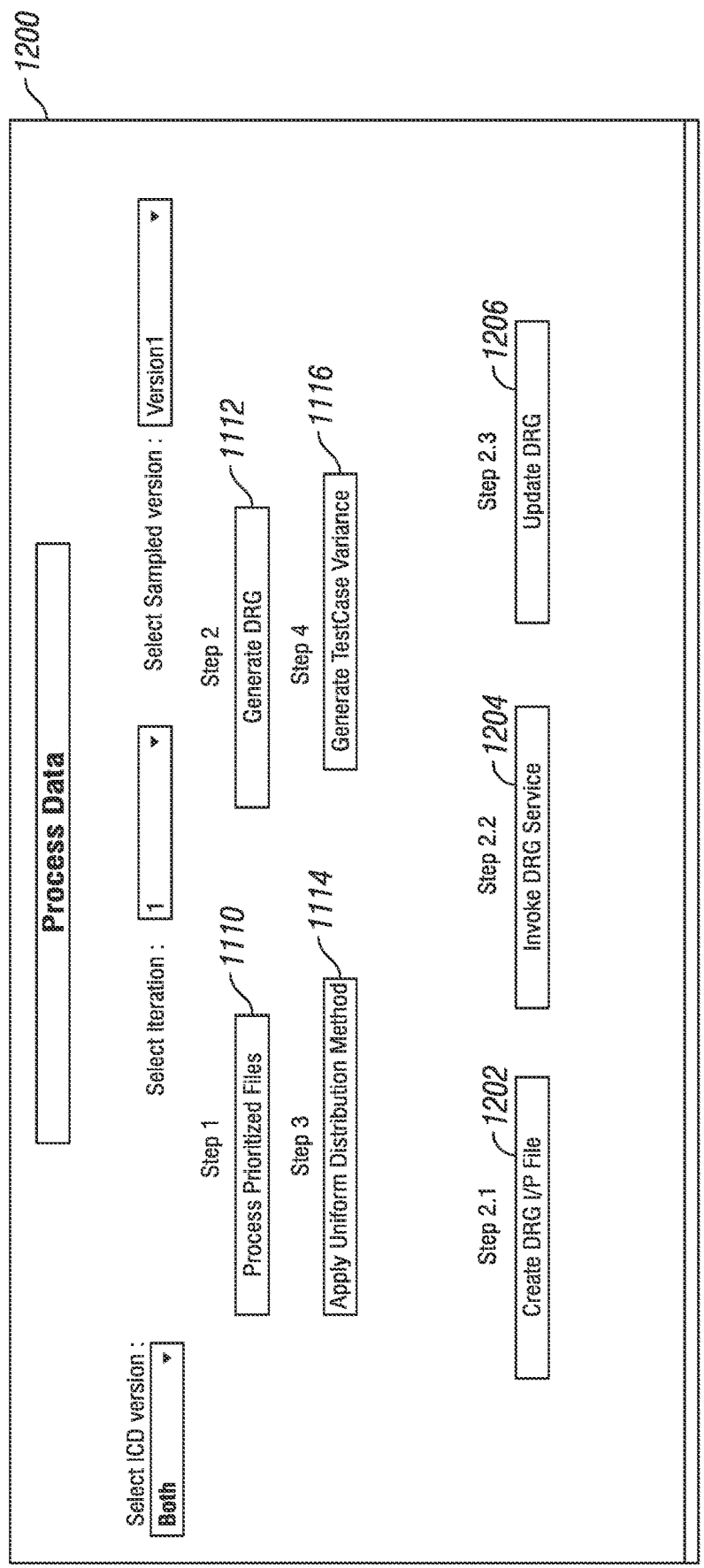
FIG. 12 is an example screen shot further illustrating the process for conducting data analysis within the tool.

Referring now to FIG. 12, an example screen shot 1200 is illustrated of a user interface for carrying out the DRG generation process 1112 using the DRG grouper 360. Illustratively the DRG generation process comprises three primary steps; creating a DRG input file 1202, invoking the DRG service described above and updating the DRG codes and weights, provider base rate information and Major Diagnostic Catetory (MDC) codes within the database. In the first step 1202, DRG grouper input and output files within the database are deleted, and DRG input data is created from claim the prioritized claim files. Illustratively, the DRG input data is created in small chunks of files rather than a large file format for the purpose of transmitting the input data to the DRG grouper 360 in small chunks or packets of files. The DRG grouper 360 may have a limit on the size of input file it can receive, or receive efficiently, and the first step 1202 in the DRG generation process 1112 therefore creates the input data in the form of a plurality of small files so that such files can be sent one-by-one to the DRG grouper, thereby making it more feasible and efficient for the DRG grouper 360 to process such input files and provide corresponding DRG output files.

In the second step 1204, the DRG service is invoked. Illustratively, the DRG service resides on an external server (e.g., PLM server) and may be illustratively be invoked remotely by the data execution module 260 of the medical claim benefit neutrality testing tool via a suitable web interface. In one embodiment, the data execution module 260 calls the DRG grouper service and illustratively passes the chunked DRG input files one-by-one to the DRG service and the DRG grouper, in turn, processes the DRG input file chunks and returns DRG output files to the data execution module. Alternatively or additionally, the data execution module 260 may call a DRG grouper package and pass the chunked DGR input files one by one to the DRG grouper 360 using a predefined package format, e.g., SSIS. In any case, in the third step 1206 the DRG grouper 360 updates the DRG codes and weights, provider base rate information and Major Diagnostic Catetory (MDC) codes, and returns the output DRG files to the data execution module 260.

Figure 13:
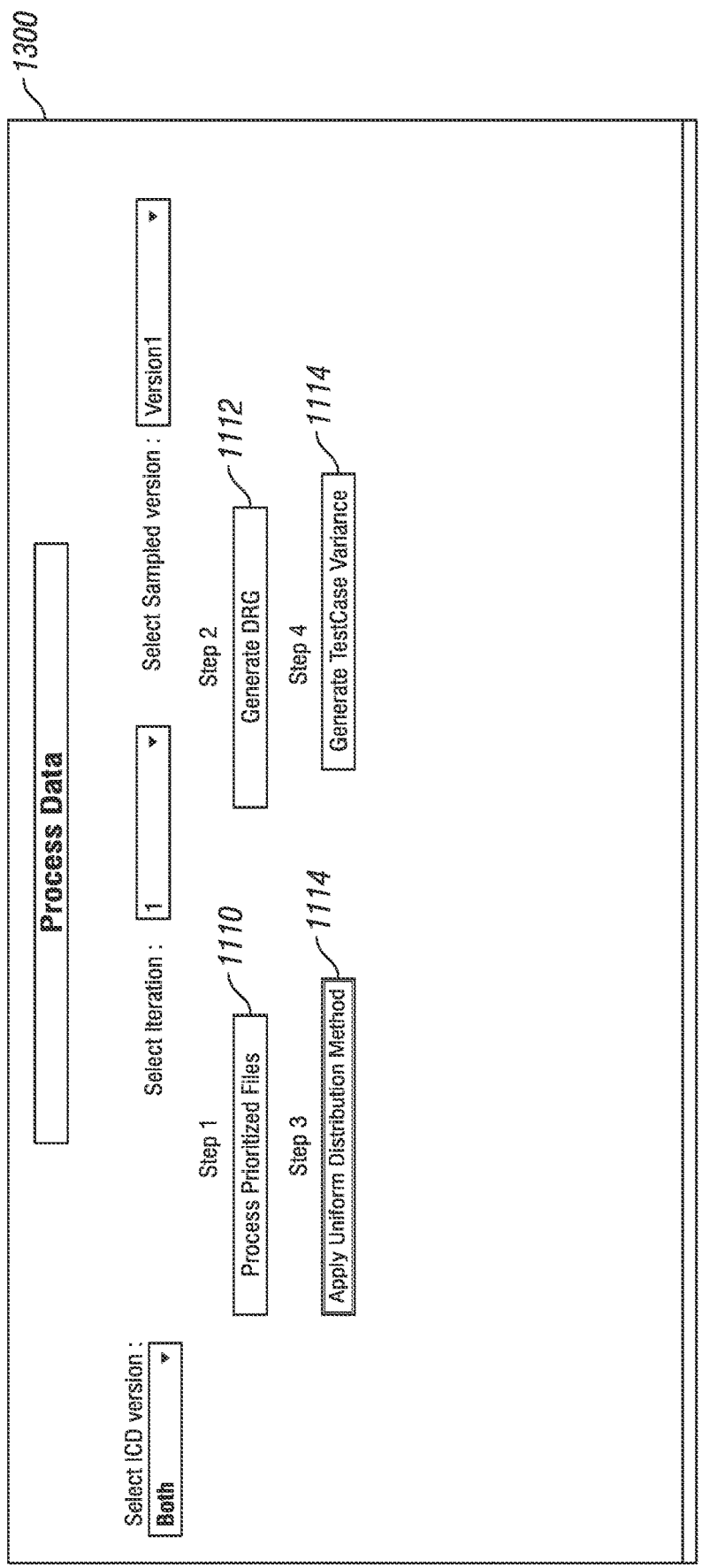
FIG. 13 is an example screen shot further illustrating the process for conducting data analysis within the tool.

Referring now to FIG. 13, following generation of the DRG codes and weights, provider base rate information and Major Diagnostic Catetory (MDC) codes, the data execution module 260 next processes the claim files to create one-to-one IDC-9 to IDC-10 mappings where such mappings are currently one-to-many so that financial and/or benefit neutrality may be directly assessed as between the IDC-9 and IDC010 code sets. In one embodiment, such data processing is undertaken by applying a uniform distribution method, or round robin method as it is sometimes called to determine the applicable IDC-9 and IDC-10 codes associated with the various claims. With the aid of the following tables, an embodiment of such a uniform distribution method will be described in a process to select one ICD-10 claim for every ICD-9 claim. As an initial step, Step 1, the ICD-9 claims record is filtered by its primary diagnosis code (PDC) as illustrated in Table V below. As indicated in Table V, the primary diagnosis code column is sorted by common PDC codes.

TABLE V

| Patient Account ID | Claim Number | Primary Diagnosis Code | Prim Proc Code |
|---|---|---|---|
| 101241684 | 101241684 | 8246 | 7936 |
| 101320643 | 101320643 | 8246 | 7936 |
| 101326548 | 101326548 | 8246 | |
| 101334733 | 101334733 | 8246 | 7926 |
| 101337879 | 101337879 | 8246 | 7936 |
| 101338230 | 101338230 | 8246 | 7926 |

The second step, Step 2, in the uniform distribution method is to choose the first PDC value and perform a lookup on the GEMs forward mapping table to determine if the code corresponds to a one-to-many mapping, and if so retrieve all of the one-to-many IDC-10 codes. In the example of Table V, the first PDC code value is 8246, and in the following example Table VI this PDC code corresponds to two IDC-10 codes S82.853A and S82.856A.

TABLE VI

| ICD-9 | ICD-10 |
|---|---|
| 824.6 | S82.853A |
| | S82.856A |

The third step, Step 3, in the uniform distribution method is to assign the first IDC-10 code value (e.g., S82.852A) for the first IDC-9-base claim number (e.g., 101241684 from Table V), and move all IDC-10 claims with the corresponding claim number and IDC-10 claim number to a temporary table, and populate a column of this table with the IDC-9 primary process code number. Table VI below is an example such temporary table.

TABLE VII

| Patient Account ID | Claim Number | IDC-10 | Prim Proc Code | ICD-9 Proc |
|---|---|---|---|---|
| 101241684 | 101241684 | S82.853A | 0QSK04Z | 7936 |
| 101241684 | 101241684 | S82.853A | 0QSG04Z | 7936 |
| 101241684 | 101241684 | S82.853A | 0QSH04Z | 7936 |
| 101241684 | 101241684 | S82.853A | 0QSJ04Z | 7936 |

The fourth step, Step 4, in the uniform distribution method is to select the second IDC-10 code (S82.856A) for the second IDC-9 claim (101320643) in Table VI and move all IDC-10 claims with claim number '101320643[' and IDC-10 code 'S82.856A' to the temporary table (i.e., Table VII).

Step 5 in the uniform distribution method is to continue the above steps 2-4 in a round-robin fashion for all one-to-many codes until allocation of records for all of the claims in the IDC-0 claim file (e.g., Table V) is complete.

Step 6 in the uniform distribution method is to apply a sort on the Primary Procedure Code column of the temporary table (Table VII), which produces the following Table VIII in the example.

TABLE VIII

| Patient Account ID | Claim Number | Primary Diagnosis Code | Prim Proc Code |
|---|---|---|---|
| 101334733 | 101334733 | 8246 | 7926 |
| 101338230 | 101338230 | 8246 | 7926 |
| 101241684 | 101241684 | 8246 | 7936 |
| 101320643 | 101320643 | 8246 | 7936 |
| 101337879 | 101337879 | 8246 | 7936 |
| 101342447 | 101342447 | 8246 | 7936 |

Step 7 in the uniform distribution method is to select the first Primary Procedure Code value (7926) in the temporary table (Table VIII) and conduct a lookup on the GEMs forward mapping table and, if the code is a one-to-many mapping, retrieve all one-to-many IDC-10 codes. In the example, this produces the following Table IX.

TABLE IX

| ICD-9 | ICD-10 |
|---|---|
| 79.26 | 0QSG0ZZ |
| | 0QSH0ZZ |
| | 0QSJ0ZZ |
| | 0QSK0ZZ |

Step 8 in the uniform distribution method is to filter the claims in the temporary table (Table VIII) on Primary Procedure Code '0QSG0ZZ' (i.e., the first one-to-many combination) and IDC-9 Primary Procedure Code '79.26,' and select the first Claim_Number record and mark it as "selected." For all of the remaining claim records with the same Claim_Number, mark them as "not selected."

Step 9 in the uniform distribution method: if there is another claim with the IDC-9 Primary Procedure Code='79.26,' filter the claims in the temporary table (Table VIII) on Primary Procedure Code32 '0QSH0ZZ' (i.e., the second one-to-many combination) and IDC-9 Primary Procedure Code='79.26.' Then select the first Claim_Number record and mark it as "selected", and for all of the remaining records with the same Claim_Number, mark them as "not selected."

Step 10 of the uniform distribution method is to continue the above steps in round-robin fashion for all of the one-to-many codes until there are no more records.

Step 11 of the uniform distribution method is to mark as "selected" all IDC-10 claims in the temporary table (Table VIII) that have a Primary Procedure Code field as blank or one-to-one.

Step 12 of the uniform distribution method is to select all records marked "selected" in the temporary table (Table VIII) and move them to a final IDC-10 claims table.

Step 13 of the uniform distribution method is to perform a reconciliation of IDC-9 to IDC-10 records and report any discrepancies as an error.

Using the first 12 steps of the foregoing uniform distribution method, a numerical example is provided in the following tables based on Table A, which is a table of IDC-9 codes sorted according to diagnosis code, Table B, which is a table of IDC-10 claims, and Table C which is a mapping table between IDC-9 to IDC-10 diagnosis codes and IDC-9 to IDC-10 procedure codes.

TABLE A

ICD9 Claims sorted on Diag

| DX | PX | Claim # |
|---|---|---|
| 256.1 | 57.94 | 101383437 |
| 256.1 | 57.94 | 101383440 |
| 256.1 | 57.94 | 101383441 |
| 387.2 | 57.94 | 101383444 |
| 387.2 | 39.95 | 101383445 |
| 387.2 | 37.22 | 101383446 |
| 387.2 | 96.72 | 101383447 |
| 808.2 | 57.94 | 101383436 |
| 808.2 | 57.94 | 101383438 |
| 808.2 | NULL | 101383439 |
| 808.2 | 57.94 | 101383442 |
| 808.2 | 37.22 | 101383443 |
| 808.2 | 57.94 | 101383448 |
| 808.2 | 96.72 | 101383449 |
| 808.2 | 57.94 | 101383450 |
| 808.2 | 96.72 | 101383451 |
| 808.2 | 57.94 | 101383452 |
| 808.2 | 96.72 | 101383453 |
| 808.2 | 37.22 | 101383454 |
| 808.2 | 57.94 | 101383455 |

TABLE B

ICD 10 Claims

| Claim # | I10 Dx | I10 Px | I9 Px |
|---|---|---|---|
| 101383436 | S32.501A | 0T9B70Z | 57.94 |
| 101383436 | S32.501A | 0T9B80Z | 57.94 |
| 101383436 | S32.502A | 0T9B70Z | 57.94 |
| 101383436 | S32.502A | 0T9B80Z | 57.94 |
| 101383436 | S32.509A | 0T9B70Z | 57.94 |
| 101383436 | S32.509A | 0T9B80Z | 57.94 |
| 101383437 | K24.203A | 0T9B70Z | 57.94 |
| 101383437 | K24.203A | 0T9B80Z | 57.94 |
| 101383437 | S56.285A | 0T9B70Z | 57.94 |

TABLE B-continued

ICD 10 Claims

| Claim # | I10 Dx | I10 Px | I9 Px |
|---|---|---|---|
| 101383437 | S56.285A | 0T9B80Z | 57.94 |
| 101383437 | S24.204A | 0T9B70Z | 57.94 |
| 101383437 | S24.204A | 0T9B80Z | 57.94 |
| 101383446 | L56.174A | 4A023N7 | 37.22 |
| 101383446 | L56.174A | 4A020N7 | 37.22 |
| 101383446 | L57.175A | 4A023N7 | 37.22 |
| 101383446 | L57.175A | 4A020N7 | 37.22 |
| 101383440 | K24.203A | 0T9B70Z | 57.94 |
| 101383440 | K24.203A | 0T9B80Z | 57.94 |
| 101383440 | S56.285A | 0T9B70Z | 57.94 |
| 101383440 | S56.285A | 0T9B80Z | 57.94 |
| 101383440 | S24.204A | 0T9B70Z | 57.94 |
| 101383440 | S24.204A | 0T9B80Z | 57.94 |
| 101383441 | K24.203A | 0T9B70Z | 57.94 |
| 101383441 | K24.203A | 0T9B80Z | 57.94 |
| 101383441 | S56.285A | 0T9B70Z | 57.94 |
| 101383441 | S56.285A | 0T9B80Z | 57.94 |
| 101383441 | S24.204A | 0T9B70Z | 57.94 |
| 101383441 | S24.204A | 0T9B80Z | 57.94 |
| 101383444 | L56.174A | 0T9B70Z | 57.94 |
| 101383444 | L56.174A | 0T9B80Z | 57.94 |
| 101383444 | L57.175A | 0T9B70Z | 57.94 |
| 101383444 | L57.175A | 0T9B80Z | 57.94 |
| 101383439 | S32.501A | NULL | NULL |
| 101383439 | S32.502A | NULL | NULL |
| 101383439 | S32.509A | NULL | NULL |

TABLE C

Translator Mapping Master

| ICD 9 - DX | ICD10- DX | ICD 9 - PX | ICD10- PX |
|---|---|---|---|
| 808.2 | S32.501A | 57.94 | 0T9B70Z |
| 808.2 | S32.502A | 57.94 | 0T9B80Z |
| 808.2 | S32.509A | 39.95 | 5A1D00Z |
| 256.1 | K24.203A | 39.95 | 5A1D60Z |
| 256.1 | S56.285A | 37.22 | 4A023N7 |
| 256.1 | S24.204A | 37.22 | 4A020N7 |
| 387.2 | L56.174A | 96.72 | 5A1955Z |
| 387.2 | L57.175A | | |

Step 1 of the uniform distribution method on the above Tables A-C is illustrated in the following Table 1:

TABLE 1

| DX | PX | Claim # |
|---|---|---|
| 256.1 | 57.94 | 101383437 |
| 256.1 | 57.94 | 101383440 |
| 256.1 | 57.94 | 101383441 |
| 387.2 | 57.94 | 101383444 |
| 387.2 | 37.22 | 101383446 |
| 808.2 | 57.94 | 101383436 |
| 808.2 | NULL | 101383439 |

Step 2 of the uniform distribution method is illustrated in the following Table 2:

TABLE 2

| ICD 9-DX | ICD10-DX |
|---|---|
| 256.1 | K24.203A |
| 256.1 | S56.285A |
| 256.1 | S24.204A |

Step 3 of the uniform distribution method is illustrated in the following Table 3:

TABLE 3

| Claim # | I10 Dx | I10 Px | I9 Px |
|---|---|---|---|
| 101383437 | K24.203A | 0T9B70Z | 57.94 |
| 101383437 | K24.203A | 0T9B80Z | 57.94 |

Steps 4-5 of the uniform distribution method are illustrated in the following Table 4:

TABLE 4

| Claim # | I10 Dx | I10 Px | I9 Px |
|---|---|---|---|
| 101383437 | K24.203A | 0T9B70Z | 57.94 |
| 101383437 | K24.203A | 0T9B80Z | 57.94 |
| 101383440 | S56.285A | 0T9B70Z | 57.94 |
| 101383440 | S56.285A | 0T9B80Z | 57.94 |
| 101383441 | S24.204A | 0T9B70Z | 57.94 |
| 101383441 | S24.204A | 0T9B80Z | 57.94 |
| 101383444 | L56.174A | 0T9B70Z | 57.94 |
| 101383444 | L56.174A | 0T9B80Z | 57.94 |
| 101383446 | L57.175A | 4A023N7 | 37.22 |
| 101383446 | L57.175A | 4A020N7 | 37.22 |
| 101383436 | S32.501A | 0T9B70Z | 57.94 |
| 101383436 | S32.501A | 0T9B80Z | 57.94 |
| 101383439 | S32.502A | NULL | NULL |

Step 6 of the uniform distribution method is illustrated in the following Table 5:

TABLE 5

| DX | PX | Claim # |
|---|---|---|
| 387.2 | 37.22 | 101383446 |
| 808.2 | 57.94 | 101383436 |
| 256.1 | 57.94 | 101383437 |
| 256.1 | 57.94 | 101383440 |
| 256.1 | 57.94 | 101383441 |
| 387.2 | 57.94 | 101383444 |
| 808.2 | NULL | 101383439 |

Step 7 of the uniform distribution method is illustrated in the following Table 6:

TABLE 6

| ICD 9 - PX | ICD10-PX |
|---|---|
| 37.22 | 4A023N7 |
| 37.22 | 4A020N7 |

Steps 8-11 of the uniform distribution method are illustrated in the following Table 7:

TABLE 7

| Claim # | I10 Dx | I10 Px | I9 Px | Selection Flag |
|---|---|---|---|---|
| 101383437 | K24.203A | 0T9B70Z | 57.94 | N |
| 101383437 | K24.203A | 0T9B80Z | 57.94 | Y |
| 101383440 | S56.285A | 0T9B70Z | 57.94 | Y |
| 101383440 | S56.285A | 0T9B80Z | 57.94 | N |
| 101383441 | S24.204A | 0T9B70Z | 57.94 | N |
| 101383441 | S24.204A | 0T9B80Z | 57.94 | Y |
| 101383444 | L56.174A | 0T9B70Z | 57.94 | Y |
| 101383444 | L56.174A | 0T9B80Z | 57.94 | N |
| 101383446 | L57.175A | 4A023N7 | 37.22 | Y |
| 101383446 | L57.175A | 4A020N7 | 37.22 | N |

TABLE 7-continued

| Claim # | I10 Dx | I10 Px | I9 Px | Selection Flag |
|---|---|---|---|---|
| 101383436 | S32.501A | 0T9B70Z | 57.94 | Y |
| 101383436 | S32.501A | 0T9B80Z | 57.94 | N |
| 101383439 | S32.502A | NULL | NULL | Y |

Finally, step 12 of the uniform distribution method is illustrated in the following Table 8:

TABLE 8

| Claim # | I10 Dx | I10 Px | I9 Px | Selection Flag |
|---|---|---|---|---|
| 101383436 | S32.501A | 0T9B70Z | 57.94 | Y |
| 101383437 | K24.203A | 0T9B80Z | 57.94 | Y |
| 101383439 | S32.502A | NULL | NULL | Y |
| 101383440 | S56.285A | 0T9B70Z | 57.94 | Y |
| 101383441 | S24.204A | 0T9B80Z | 57.94 | Y |
| 101383444 | L56.174A | 0T9B70Z | 57.94 | Y |
| 101383446 | L57.175A | 4A023N7 | 37.22 | Y |

As illustrated in Table 8, the each of the claims originally having a one-to-many mapping between IDC-9 and IDC-10 codes now has a one-to-one mapping of IDC-9 to IDC-10 codes.

In assessing benefit and/or financial neutrality, it is desirable to compare each IDC-9 Grouper amount against a single corresponding IDC-10 grouper amount in order to properly quantify and track the actual variances between the two code sets IDC-9 and IDC-10. Unless such one-to-one comparisons are made, such variance calculations would lead to inaccurate results. As an example, consider the case where IDC-9 codes are not separated from one-to-many mappings of IDC-10 codes. Variance calculations under such circumstances may improperly take into account the multiple claim count of the "many" IDC-10 mappings to a single IDC-9 code, which claim count may erroneously be included in the total IDC-9 grouper amount Calculations on real-world data have shown that such inaccurate techniques for computing variances lead, on one set of data, to a −16.98% variance between the calculated total IDC-9 Grouper amount and the calculated total IDC-10 Grouper amount, whereas by using the uniform distribution method illustrated and described herein the variance between the calculated total IDC-9 Grouper amount and the calculated total IDC-10 Grouper amount was −12.17%. With large sets of real world claims, several percentage points in variance may translate to large monetary amounts and/or large differences in benefits.

For cases defined in the above mentioned data management tool, embodiments of the present disclosure compute variances according to different scenarios and mappings. The computed variances are compared to pre-set thresholds (e.g., maximum variances) to assess whether certain test cases would be considered a success under the ICD-10 migration (e.g., below the threshold value), or a failure (e.g., above the threshold value). The failure test cases would be further analyzed under a data verification phase to understand exactly why the claim failed.

According to embodiments of the present disclosure, in the data analytics phase, the neutrality testing system provides a comprehensive set of pre-defined analytical reports enabling users to understand and analyze the monetary variances resulting between ICD-9 and ICD-10 coded claim files according to the user's (e.g., healthcare organization's current practices). The system provides reports illustrating allowed amounts, paid amounts, member co-pay amounts, member co-insurance amounts, and member deductible amounts per department or line of business. These reports provide insight on trends across cycles, risk identification, and help a user derive mitigation plans to ensure neutrality in the transition to ICD-10 code.

Figure 14:
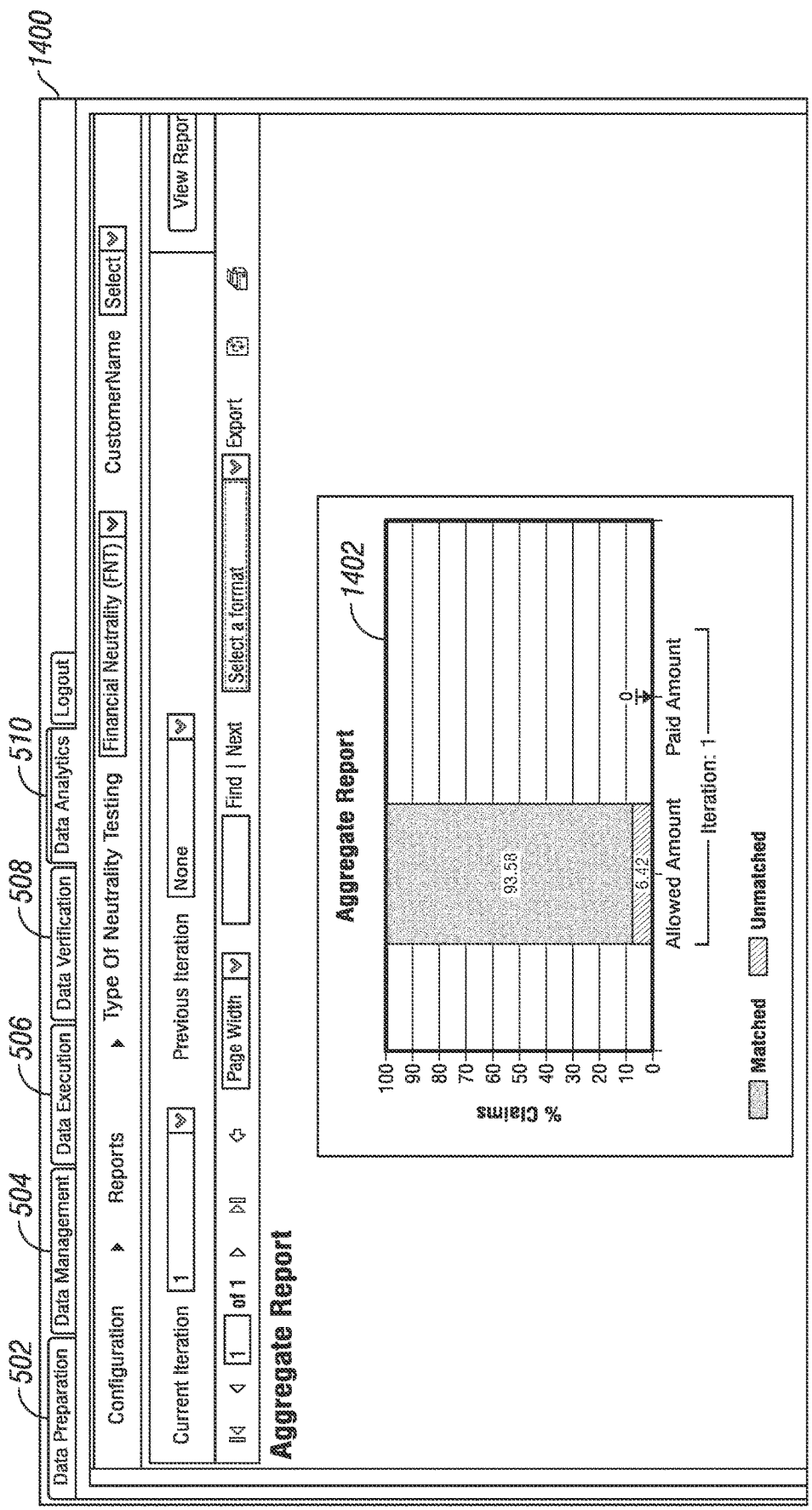
FIG. 14 is an example screen shot illustrating an example aggregate report generated by the tool.

As shown in the example screen shot in FIG. 14, under the data analytics tab 510, the system allows the user to view a report 1402 showing an allowed amount and a paid amount for a given test case set (e.g., iteration, type of neutrality testing selected and customer). This report analyzes all the ICD-9 coded claims and the mapped ICD-10 coded claims for a given iteration. In the embodiment shown, this report illustrates a percentage of the mapped claims where the allowed amount and paid amount has not changed due to the mapping (i.e., the allowed amount for the ICD-9 coded claim "matches" the allowed amount for the mapped ICD-10 coded claim); as well as a percentage of the mapped claims where the allowed amount has changed due to the mapping (i.e., the allowed amount is "unmatched" for the mapped ICD-10 claim). This report aids a user in understanding an overall percentage shift in allowed and paid amounts for a total set of claims. Benefit neutrality analysis may be performed for additional categories such as member co-insurance amount, co-pay amount, and deductible amount.

Figure 15:
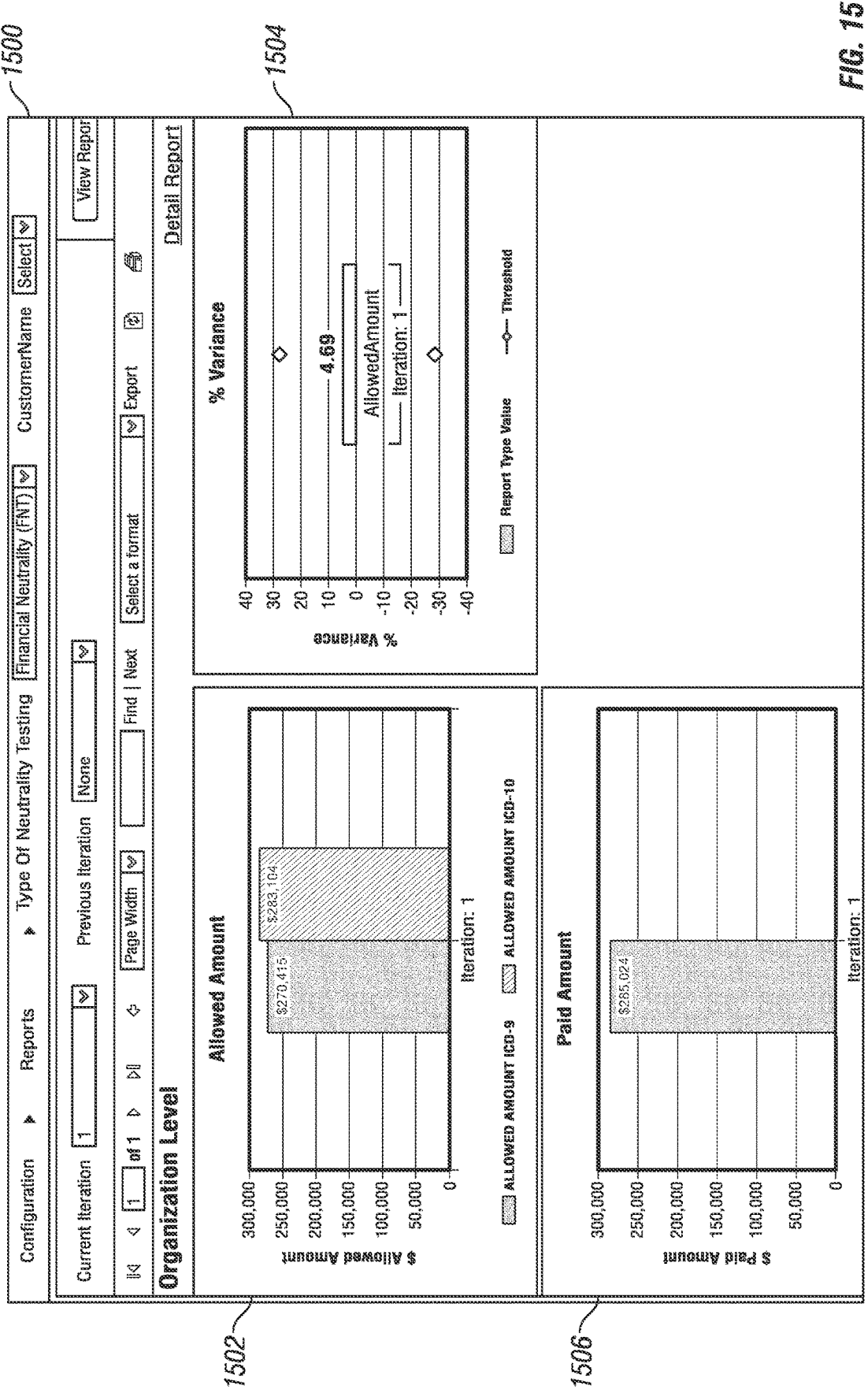
FIG. 15 is an example screen shot illustrating an example organization level report generated by the tool.

As shown in the example screen shot in FIG. 15, embodiments of the present disclosure include reports that provide a breakdown of the actual allowed amounts 1502 per ICD coded claim type (i.e., ICD-9 coded claim or ICD-10 coded claim), percent variance and threshold variance 1504 of the allowed amounts between the two claim types, as well as the total paid amount 1506 for ICD-9 coded claims.

Figure 16:
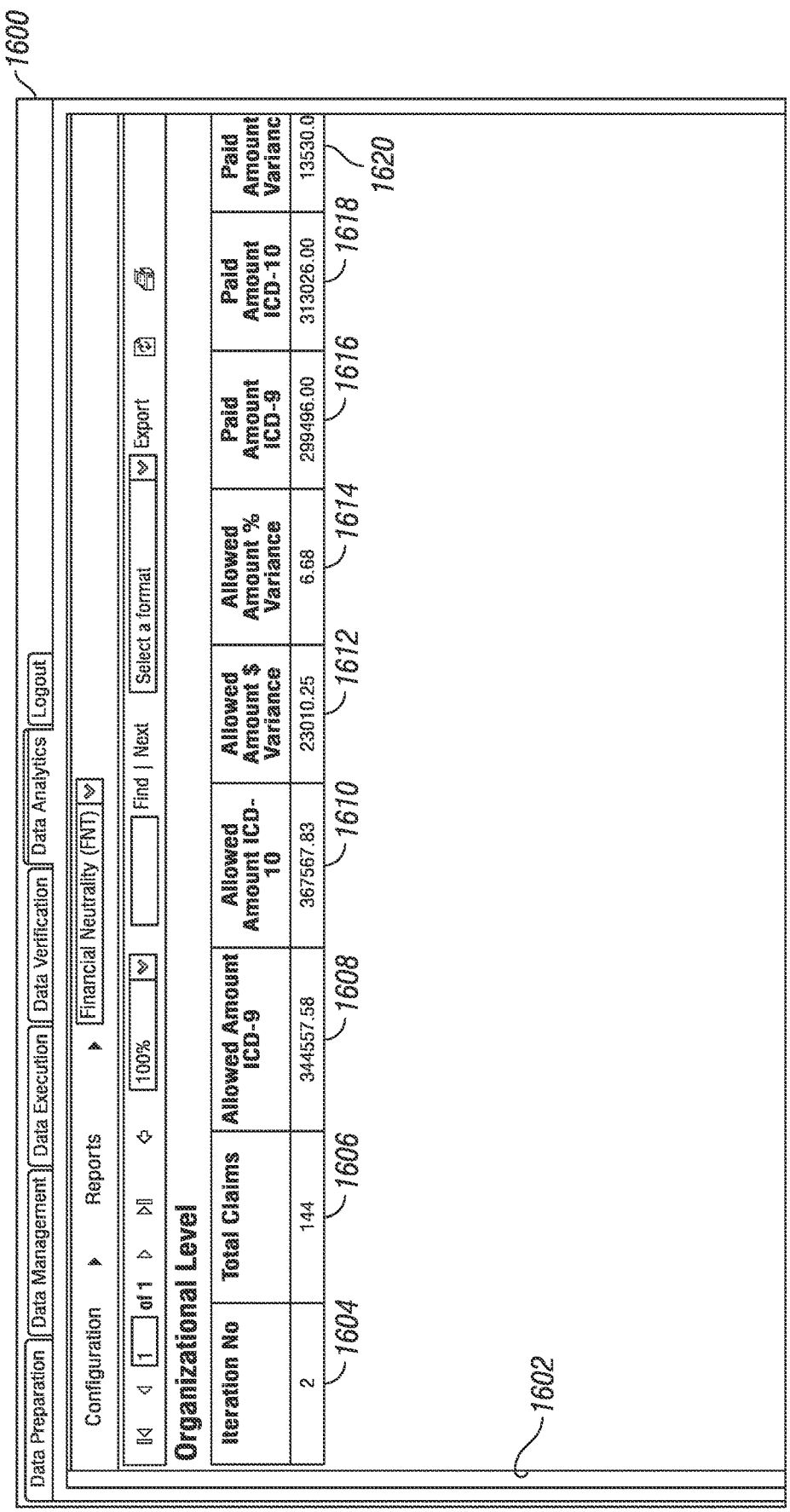
FIG. 16 is an example screen shot illustrating an example detail organization level report generated by the tool.

Referring to the example screen shot in FIG. 16, a detailed report 1602 can also be presented which lists claim details per iteration including: the iteration number 1604, total claims in the specified iteration 1606, a total allowed amount for the ICD-9 claims 1608, a total allowed amount for the ICD-10 claims 1610, the amount of variance between these allowed amounts 1612, the percentage variance between the allowed amounts 1614, a paid amount for the ICD-9 claims 1616, a paid amount for the ICD-10 claims 1618, and an amount of variance between these two paid amounts 1620.

Figure 17A:
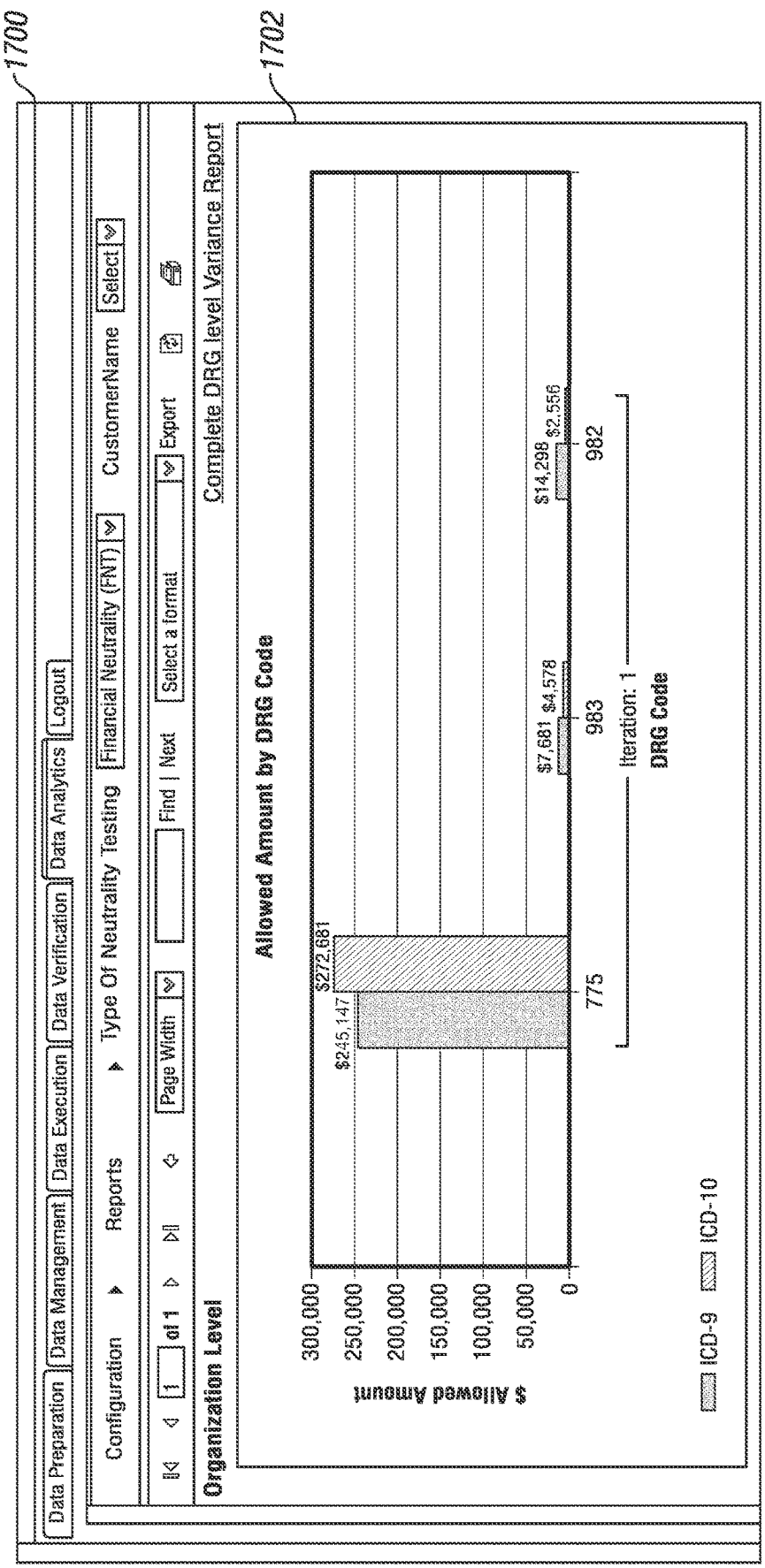
FIG. 17A is an example screen shot illustrating an example DRG allowed amount report generated by the tool.
Figure 17B:
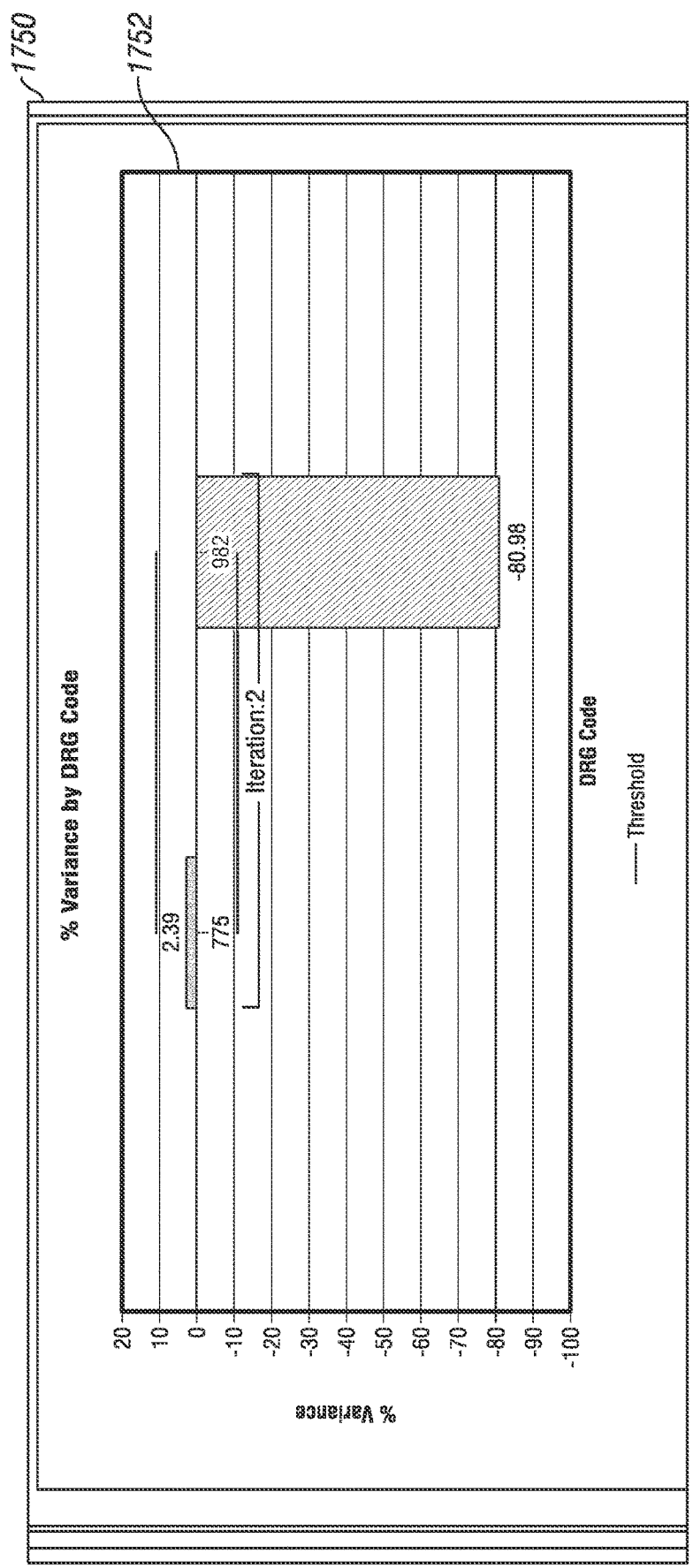
FIG. 17B is an example screen shot illustrating an example percent variance by DRG code report generated by the tool.

FIG. 17A is an example screen shot 1700 displayed if the user selected to view a comparison 1702 of a total allowed amount of ICD-9 and mapped ICD-10 claims per DRG code. FIG. 17B is an example screen shot 1750 showing percent variances 1754 between the respective ICD-9 and mapped ICD-10 allowed amounts per DRG code.

Figure 18A:
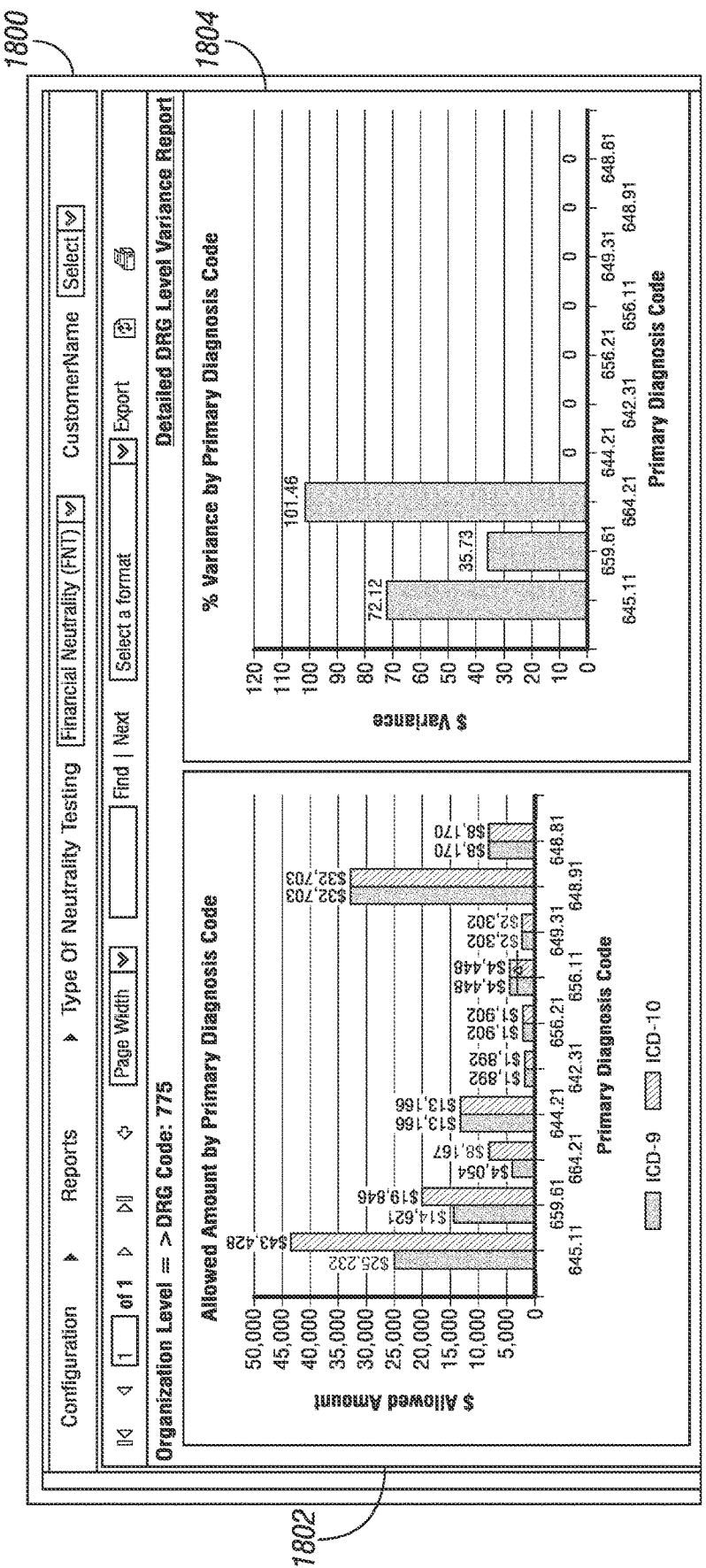
FIG. 18A is an example screen shot illustrating an example allowed amount by primary diagnosis code and percent variance report generated by the tool.
Figure 18B:
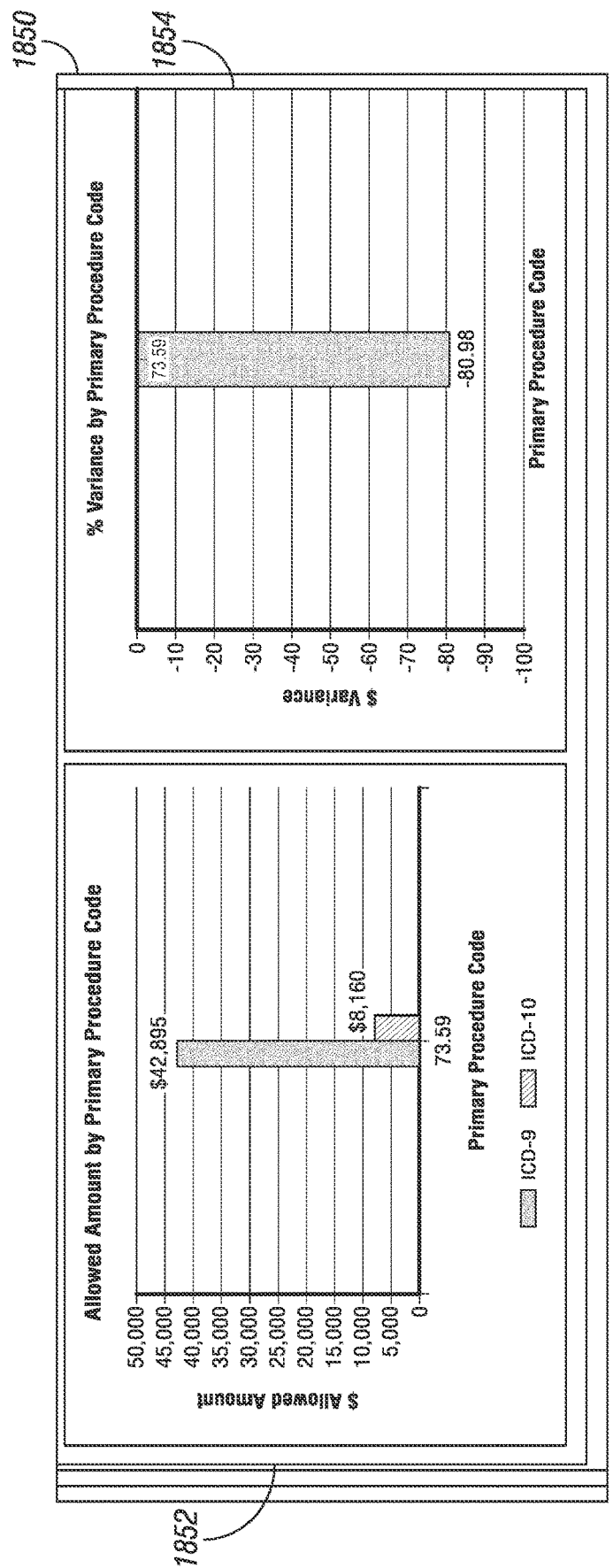
FIG. 18B is an example screen shot illustrating an example allowed amount by primary procedure code and percent variance report generated by the tool.

As discussed above, there are ICD (i.e., "ICD-9 and ICD-10") diagnosis codes as well as ICD procedure codes. As such, embodiments of the present disclosure allow a user to view reports similar to above, except now with respect to these particular ICD diagnosis and procedure codes. For example, as shown in the example screen shot 1800 in FIG. 18A, reports are shown providing a breakdown of the actual allowed amounts 1802 per ICD diagnosis codes (i.e., ICD-9 coded claim or ICD-10 coded claim), and percent variance 1804 of the allowed amounts between the two claim types. Likewise, the screen shot 1850 illustrated in FIG. 18B also reports providing a bar chart 1852 showing actual allowed amounts per ICD procedure codes (i.e., ICD-9 coded claim or ICD-10 coded claim), and a bar chart 1854 showing percent variance of the allowed amounts between the two claim types.

FIG. 19 is an example screen shot 1900 with a detailed report showing details of ICD-9 1902 and mapped ICD-10 coded claims 1904 per iteration. In this example, the presentation is consistent with that shown in FIG. 16, except this report shows the information with respect to the noted DRG codes, procedure codes, and diagnosis codes.

Figure 20:
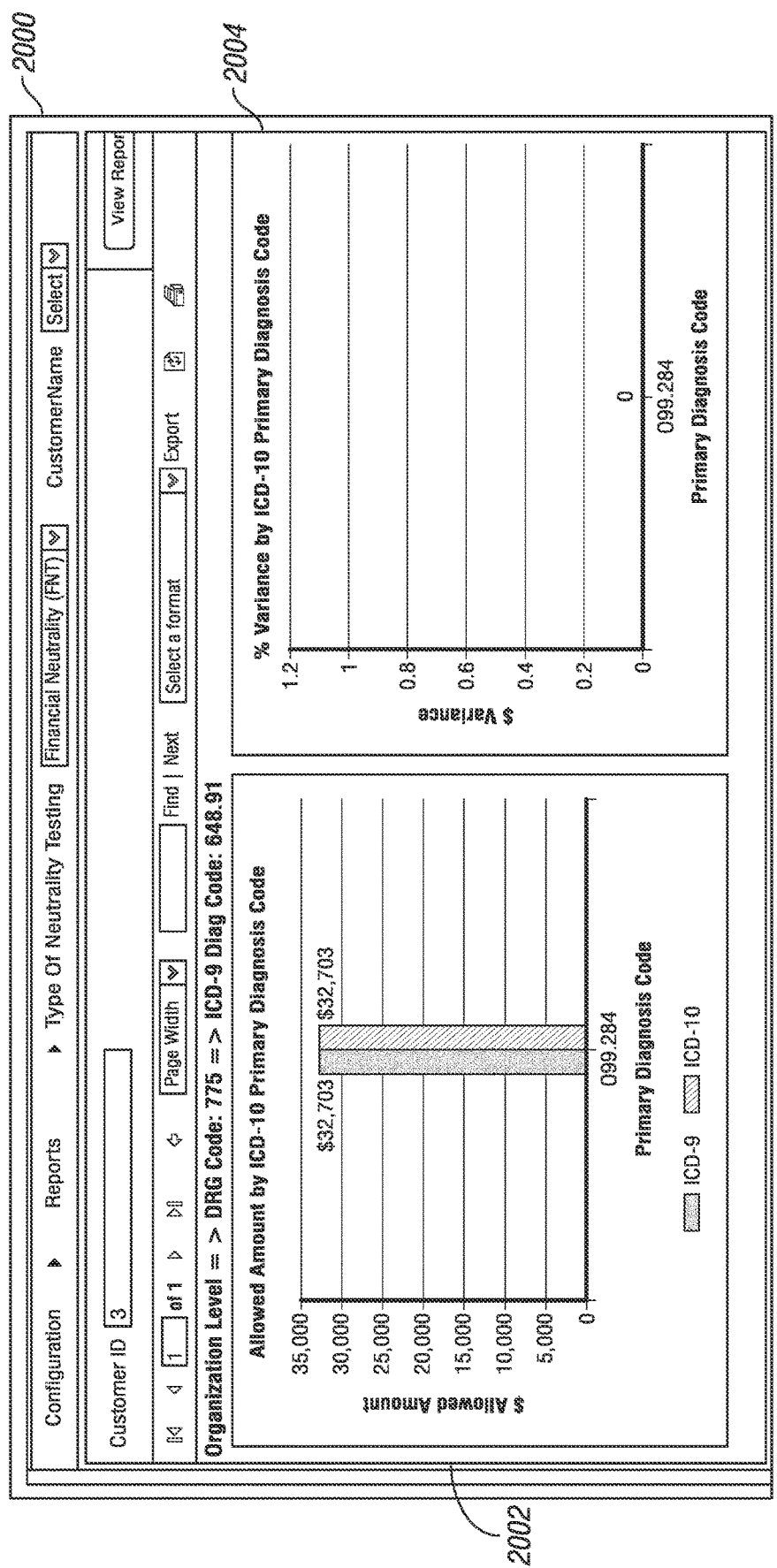
FIG. 20 is an example screen shot illustrating an example allowed amount by ICD-10 primary diagnosis code and percent variance report generated by the tool.

As discussed herein, mappings between ICD-9 codes and ICD-10 codes can be one-to-one, one-to-many, and the like. The screen shot 2000 illustrated in FIG. 20 shows an example bar chart 2002 showing allowed amount variance by ICD-9 diagnosis code. This report helps to understand the ICD-9 code that is causing the shift in allowed amount.

It should be noted that a drill down report may allow a user to select the filtering criteria for analysis of the reports discussed herein. The user may select different levels of the filtration criteria, and corresponding values. For example, the user can perform analysis on the parameters such as line of business, platform code, provider state, place of service, and the like.

Figure 21:
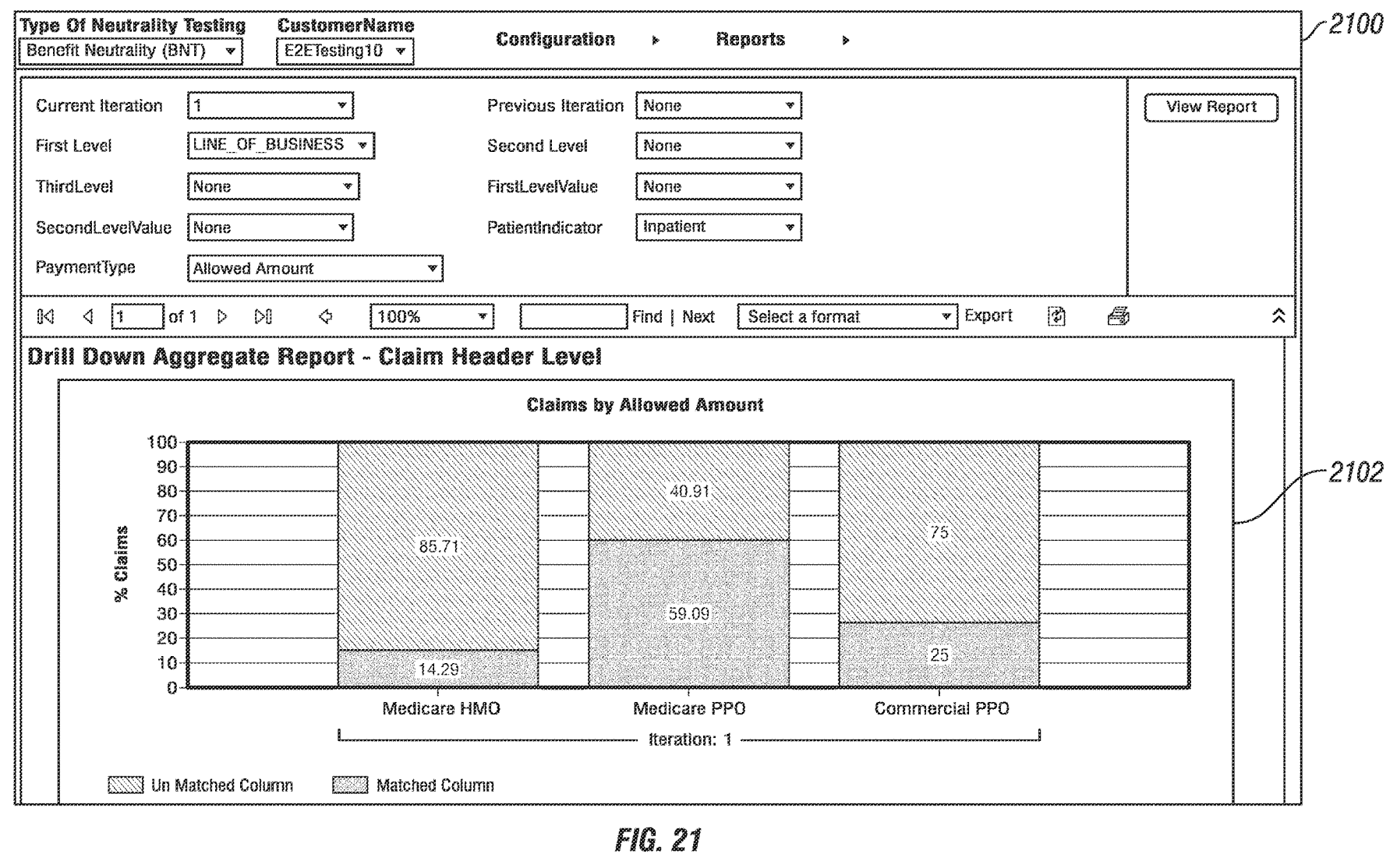

FIG. 21 is an example screen shot 2100 if the user desires to view a drill down report 2102 showing an allowed amount and a paid amount by filtering criteria's like Line of Business, Provider, etc. in the selected iteration.

Figure 22A:
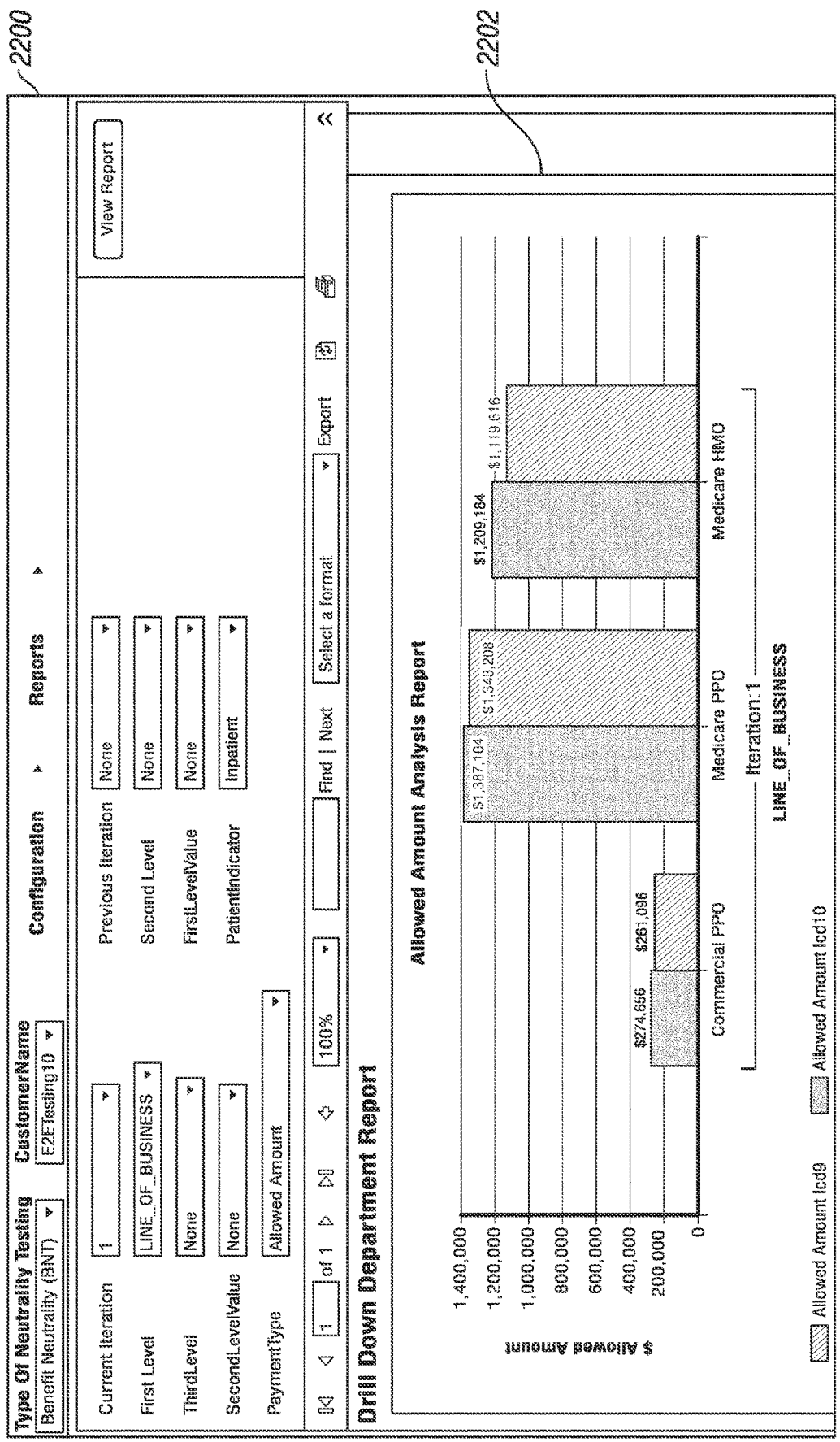
FIG. 22A is an example screen shot illustrating an example allowed amount report by DRG code.
Figure 22B:
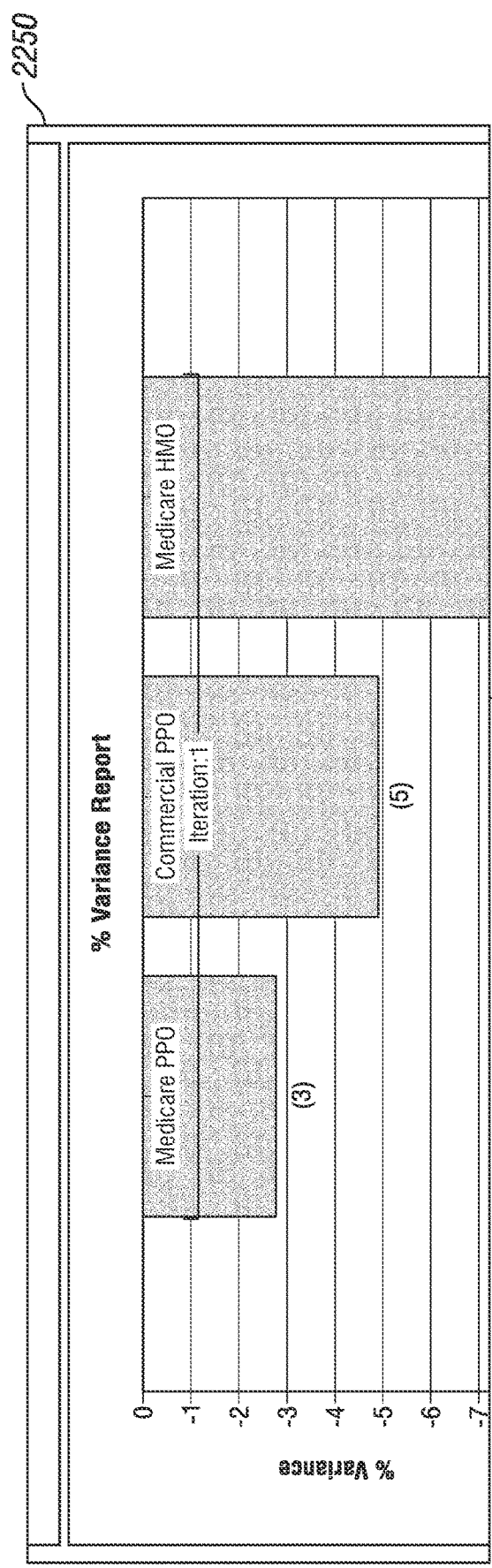
FIG. 22B is an example screen shot illustrating an example percent variance report corresponding to the report illustrated in FIG. 22A.

The screen shot 2200 illustrated in FIG. 22A is an example screen shot if the user desires to view a report 2202 showing a bar chart of the actual allowed amounts per DRG code with respect to filtered criteria's like Line of Business, Provider, etc. in the selected iteration. In this example, the report is consistent with that shown in FIG. 15, except showing the information with respect to the age of the member of each claim in the selected iteration. The screen shot 2250 illustrated in FIG. 22B is an example report 2252 illustrating a percent variance in relation to the report 2202 of FIG. 22A.

The screen shot 2300 illustrated in FIG. 23 is an example heat map report displaying the payment percent variation for the most used DRG Codes (e.g., the top 15) for a particular iteration, and other details about each of these descriptions for each of ICD-9 claims 2302 and ICD-10 claims 2304. By knowing the most used descriptions, the user/organization can focus on those areas. Specifically, with the help of the system, an organization can hone in on the areas where the percent variance is greatest, and, thus, select particular mappings for ICD codes that put the user or organization in the most financially neutral position with respect to the ICD migration.

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:

1. A computerized method comprising:
receiving existing claim data including at least one existing healthcare code associated with a first classification system;
receiving new claim data including at least one new healthcare code associated with a second classification system, wherein the at least one existing healthcare code is mapped to the at least one new healthcare code;
receiving a plurality of payment codes associated with the at least one existing healthcare code and the at least one new healthcare code;
converting, using a processor, a one-to-many mapping from said at least one existing healthcare code associated with the first classification system to a plurality of said new healthcare codes associated with the second classification system, to a corresponding plurality of one-to-one mappings from said at least one existing healthcare code associated with the first classification system to one of said plurality of said new healthcare codes associated with the second classification system;

based upon the plurality of one-to-one mappings and the plurality of payment codes, generating a test case, the test case defined by at least one payment variance threshold and at least one benefit variance threshold;

based on the received plurality of payment codes, calculating payments and benefits of the received existing and new claim data, respectively, wherein the calculating payments further comprises calculating a respective variance between the calculated payments and benefits of the received existing and new claim data;

executing the test case to determine whether the calculated payment variance exceeds the at least one payment variance threshold, wherein if the calculated payment variance exceeds the at least one payment variance threshold, the test case is further executed to determine an allowed amount variance and a paid amount variance;

executing the test case to determine whether the calculated benefit variance between the calculated benefits of the received existing and new claim data exceeds the at least one benefit variance threshold; and providing a user interface configured to receive a user selection of a financially neutral new healthcare code of the at least one new healthcare codes, wherein providing the user interface comprises:
 based upon the calculation of the payment variance, identifying the at least one existing healthcare code or the at least one new healthcare code causing the payment variance;
 based upon historical user selection information, identifying the most used new healthcare code identified by the one-to-one mappings; and
 generating a report comprising:
  (i) the identification of the at least one existing healthcare code or the at least one new healthcare code causing the payment variance; and
  (ii) the most used new healthcare code identified by the one-to-one mappings.

2. The computerized method of claim 1, wherein the payments comprise an amount a healthcare provider is allowed to receive for a rendered service.

3. The computerized method of claim 1, wherein the payments comprise an amount paid by an insured patient for receiving a service from a healthcare provider, wherein the insured patient is associated with the existing and new claim data.

4. The computerized method of claim 1, wherein the calculating further comprises calculating payments of the received existing and new claim data with respect to an age of an insured patient associated with the existing and new claim data.

5. The computerized method of claim 1, wherein the calculating the payment variance is with respect to an age of an insured patient associated with the existing and new claim data.

6. The computerized method of claim 1, wherein the plurality of payment codes are diagnosis related group ("DRG") codes.

7. The computerized method of claim 1, wherein if the calculated variance between the calculated benefits of the received existing and new claim data exceeds the at least one benefit variance threshold, the test case is further executed to determine a deductible variance, a gender restriction variance, and an age limitation variance.

8. The computerized method of claim 7, wherein based upon the calculation of the benefits variance, identifying the at least one existing healthcare code or the at least one new healthcare code causing the benefits variance.

9. The computerized method of claim 8, the generating a report further comprising the identification of the at least one existing healthcare code or the at least one new healthcare code causing the benefit variance.

10. A system comprising:
 one or more computing devices including:
  a memory having program code stored therein;
  a processor in communication with the memory for carrying out instructions in accordance with the stored program code, wherein the program code, when executed by the processor, causes the processor to perform steps comprising:
   receiving existing claim data including at least one existing healthcare code associated with a first classification system;
   receiving new claim data including a plurality of new healthcare codes associated with a second classification system, wherein the at least one existing healthcare code is mapped to the at least one new healthcare code;
   receiving a plurality of payment codes associated with the at least one existing healthcare code and the at least one new healthcare code;
   converting, using a processor, a one-to-many mapping from said at least one existing healthcare code associated with the first classification system to a plurality of said new healthcare codes associated with the second classification system, to a corresponding plurality of one-to-one mappings from said at least one existing healthcare code associated with the first classification system to one of said plurality of said new healthcare codes associated with the second classification system;
   based upon the plurality of one-to-one mappings and the plurality of payment codes, generating a test case, the test case defined by at least one payment variance threshold and at least one benefit variance threshold;
   based on the received plurality of payment codes, calculating payments and benefits of the received existing and new claim data, respectively, wherein the calculating payments further comprises calculating a respective variance between the calculated payments and benefits of the received existing and new claim data;
   executing the test case to determine whether the calculated payment variance exceeds the at least one payment variance threshold, wherein if the calculated payment variance exceeds the at least one payment variance threshold, the test case is further executed to determine an allowed amount variance and a paid amount variance;
   executing the test case to determine whether the calculated benefit variance between the calculated benefits of the received existing and new claim data exceeds the at least one benefit variance threshold; and
   providing a user interface configured to receive a user selection of a financially neutral new healthcare code of the at least one new healthcare codes, wherein providing the user interface comprises:

based upon the calculation of the payment variance, identifying the at least one existing healthcare code or the at least one new healthcare code causing the payment variance;

based upon historical user selection information, identifying the most used new healthcare code identified by the one-to-one mappings; and generating a report comprising:
  (i) the identification of the at least one existing healthcare code or the at least one new healthcare code causing the payment variance; and
  (ii) the most used new healthcare code identified by the one-to-one mappings.

11. The system of claim 10, wherein the payments comprise an amount a healthcare provider is allowed to receive for a rendered service.

12. The system of claim 10, wherein the payments comprise an amount paid by an insured patient for receiving a service from a healthcare provider, wherein the insured patient is associated with the existing and new claim data.

13. The system of claim 10, wherein the calculating further comprises calculating payments of the received existing and new claim data with respect to an age of an insured patient associated with the existing and new claim data.

14. The system of claim 10, wherein the calculating the payment variance is with respect to an age of an insured patient associated with the existing and new claim data.

15. The system of claim 10, wherein the plurality of payment codes are diagnosis related group ("DRG") codes.

16. A non-transitory computer readable medium upon which is embodied a sequence of programmed instructions which, when executed by a processor, cause the processor to perform steps comprising:

receiving existing claim data including at least one existing healthcare code associated with a first classification system;

receiving new claim data including a plurality of new healthcare codes associated with a second classification system, wherein the at least one existing healthcare code is mapped to the at least one new healthcare code;

receiving a plurality of payment codes associated with the at least one existing healthcare code and the at least one new healthcare code;

converting, using a processor, a one-to-many mapping from said at least one existing healthcare code associated with the first classification system to a plurality of said new healthcare codes associated with the second classification system, to a corresponding plurality of one-to-one mappings from said at least one existing healthcare code associated with the first classification system to one of said plurality of said new healthcare codes associated with the second classification system;

based upon the plurality of one-to-one mappings and the plurality of payment codes, generating a test case, the test case defined by at least one payment variance threshold and at least one benefit variance threshold;

based on the received plurality of payment codes, calculating payments and benefits of the received existing and new claim data, respectively, wherein the calculating payments further comprises calculating a respective variance between the calculated payments and benefits of the received existing and new claim data; and executing the test case to determine whether the calculated payment variance exceeds the at least one payment variance threshold, wherein if the calculated payment variance exceeds the at least one payment variance threshold, the test case is further executed to determine an allowed amount variance and a paid amount variance;

executing the test case to determine whether the calculated benefit variance between the calculated benefits of the received existing and new claim data exceeds the at least one benefit variance threshold; and providing a user interface configured to receive a user selection of a financially neutral new healthcare code of the at least one new healthcare codes, wherein providing the user interface comprises:

based upon the calculation of the payment variance, identifying the at least one existing healthcare code or the at least one new healthcare code causing the payment variance;

based upon historical user selection information, identifying the most used new healthcare code identified by the one-to-one mappings; and generating a report comprising:
  (i) the identification of the at least one existing healthcare code or the at least one new healthcare code causing the payment variance; and
  (ii) the most used new healthcare code identified by the one-to-one mappings.

17. The non-transitory computer readable medium of claim 16, wherein the payments comprise an amount a healthcare provider is allowed to receive for a rendered service.

18. The non-transitory computer readable medium of claim 16, wherein the payments comprise an amount paid by an insured patient for receiving a service from a healthcare provider, and wherein the insured patient is associated with the existing and new claim data.

19. The non-transitory computer readable medium of claim 16, further comprising calculating payments of the received existing and new claim data with respect to an age of an insured patient associated with the existing and new claim data.

20. The non-transitory computer readable medium of claim 16, wherein the calculating the payment variance is with respect to an age of an insured patient associated with the existing and new claim data.

* * * * *